United States Patent
Gant et al.

(10) Patent No.: US 10,562,951 B2
(45) Date of Patent: Feb. 18, 2020

(54) PROCESS FOR PREPARING RECOMBINANT INSULIN USING MICROFILTRATION

(71) Applicants: Merck Sharp & Dohme Corp., Rahway, NJ (US); Sean S. Gant, Elkton, VA (US); Michael J. Iammarino, Kenilworth, NJ (US); Kristi Kerchner, Elkton, VA (US); Michael A. Rauscher, Kenilworth, NJ (US); David J. Roush, Kenilworth, NJ (US); Christopher H. Smith, Miami, FL (US); Martin Chandler, Palo Alto, CA (US); Matthew Petroff, Baltimore, MD (US)

(72) Inventors: Sean S. Gant, Elkton, VA (US); Michael J. Iammarino, Kenilworth, NJ (US); Kristi Kerchner, Elkton, VA (US); Michael A. Rauscher, Kenilworth, NJ (US); David J. Roush, Kenilworth, NJ (US); Christopher H. Smith, Miami, FL (US); Martin Chandler, Palo Alto, CA (US); Matthew Petroff, Baltimore, MD (US)

(73) Assignee: Merck Sharp & Dohme Corp., Rahway, NJ (US)

(*) Notice: Subject to any disclaimer, the term of this patent is extended or adjusted under 35 U.S.C. 154(b) by 42 days.

(21) Appl. No.: 15/556,511

(22) PCT Filed: Mar. 3, 2016

(86) PCT No.: PCT/US2016/020534
§ 371 (c)(1),
(2) Date: Sep. 7, 2017

(87) PCT Pub. No.: WO2016/144658
PCT Pub. Date: Sep. 15, 2016

(65) Prior Publication Data
US 2018/0044395 A1    Feb. 15, 2018

Related U.S. Application Data

(60) Provisional application No. 62/130,690, filed on Mar. 10, 2015.

(51) Int. Cl.
C07K 14/62 (2006.01)
C07K 1/34 (2006.01)
C12P 21/06 (2006.01)

(52) U.S. Cl.
CPC .......... C07K 14/62 (2013.01); C07K 1/34 (2013.01); C12P 21/06 (2013.01)

(58) Field of Classification Search
CPC .......... A61K 2039/505; A61K 38/195; A61K 2300/00; A61K 38/00; C07K 1/18; C07K 16/065; C07K 1/36; C07K 1/22; C07K 16/088; C07K 16/18; C07K 16/244; C07K 16/40; C07K 2317/24; C07K 2317/51; C07K 2317/515; C07K 2317/56; C07K 2317/565; C07K 1/34; C07K 16/2878; C07K 1/30; C07K 1/32; C07K 14/58; C07K 14/62; C07K 1/16; C07K 1/165; C07K 2319/02; C07K 2319/50; C07K 2319/61; C07K 2319/75; C07K 14/245; C07K 14/70521; C07K 16/1232; C07K 16/2818; C07K 2317/73; C07K 2317/76; C07K 2319/30; C07K 16/00; C07K 2317/14; C07K 16/2845; B01D 15/3804; B01D 15/327; B01D 15/363; B01D 15/14; B01D 15/3847; B01D 15/424; C12N 15/625; C12N 9/90; C12N 2510/02; C12N 2511/00; C12N 5/0018; C12P 21/06; C12P 21/00; G01N 30/461; G01N 33/563; G01N 33/6812; C12Y 502/01008; C12M 29/04; C12M 29/10; C12M 29/16; C12M 33/14

See application file for complete search history.

(56) References Cited

U.S. PATENT DOCUMENTS

| | | |
|---|---|---|
| 2006/0234226 A1 | 10/2006 | Fahner et al. |
| 2011/0117600 A1 | 5/2011 | Annibali et al. |
| 2011/0257091 A1 | 10/2011 | DiMarchi et al. |
| 2012/0058513 A1* | 3/2012 | Lazaryev ............... C07K 14/62 435/69.4 |
| 2014/0170702 A1 | 6/2014 | Reitmeir et al. |
| 2014/0235537 A1 | 8/2014 | Meehl et al. |

FOREIGN PATENT DOCUMENTS

| | | |
|---|---|---|
| DE | 19825447 A1 | 12/1999 |
| WO | WO0027869 A1 | 5/2000 |
| WO | WO03102132 A2 | 12/2003 |
| WO | WO06105426 A2 | 10/2006 |
| WO | W02014122651 | 8/2014 |

OTHER PUBLICATIONS

Barackman et al., Evaluation of on-line high-performance size-exclusion chromatography, differential refractometry, and multi-angle laser light scattering analysis for the monitoring of the oligomeric state of human immunodeficiency virus vaccine protein antigen, Journal of Chromatography A, 2004, vol. 1043(1) pp. 57-64.

(Continued)

*Primary Examiner* — Deborah K Ware
(74) *Attorney, Agent, or Firm* — John David Reilly; Anna L. Cocuzzo

(57) ABSTRACT

The use of two tandem microfiltration (MF) steps in a process for making recombinant insulin is described. The two MF steps in a single downstream purification unit operation reduce both soluble and insoluble impurities and exchange the insulin product into a suitable buffer for downstream purification.

15 Claims, 10 Drawing Sheets

Specification includes a Sequence Listing.

(56) References Cited

OTHER PUBLICATIONS

Belfort et al., The behavior of suspensions and macromolecular solutions in crossflow microfiltration, Journal of Membrane Science, 1994, vol. 96(1-2) pp. 1-58.
Bentham et al., Protein Precipitate Recovery Using Microporous Membranes, Biotechnology and Bioengineering,1988, vol. 31(9), pp. 984-994.
Bramaud et al., Whey Protein Fractionation: Isoelectric Precipitation of alpha-Lactalbumin under Gentle Heat Treatment, Biotechnology and Bioengineering, 1997, vol. 56(4), pp. 391-397.
Fahrner et al., Real-time control of antibody loading during protein A affinity chromatography using an on-line assay, Journal of Chromatography A, 1999, vol. 849, pp. 191-196.
Gagnon et al., Technology trends in antibody purification, Journal of Chromatography A, 2012, vol. 1221, pp. 57-70.
Ge et al., Purification of an Elastin-Like Fusion Protein by Microfiltration, Biotechnology and Bioengineering, 2006, vol. 95(3) pp. 424-432.
Ho et al., A Combined Pore Blockage and Cake Filtration Model for Protein Fouling during Microfiltration, Journal of Colloid and Interface Science, 2000, vol. 232(2) pp. 389-399.
Kim et al., Effect of Pump Shear on the Performance of a Crossflow Membrane Bioreactor, Water Research, 2001, vol. 35(9) pp. 2137-2144.
Kim et al., Some Factors Determining Protein Aggregation during Ultra filtration, Biotechnology and Bioengineering, 1993, vol. 42(2) pp. 260-265.
Kovacs et al., Numerical simulation and optimization of multi-step batch membrane processes, Journal of Membrane Science, 2008, vol. 324(1-2), pp. 50-58.
Lutz et al., Ultrafiltration Process Design and Implementation, Process Scale Bioseparations for the Biopharmaceutical Industry, 2007, vol. 10, pp. 297-332.
Maa et al., Protein Denaturation by Combined Effect of Shear and Air-Liquid Interface, Biotechnology and Bioengineering, 1997, vol. 54(6) pp. 503-512.
Marichal-Gallardo et al., State-of-the-Art in Downstream Processing of Monoclonal Antibodies: Process Trends in Design and Validation, Biotechnology Prog. 2012, vol. 28(4) pp. 899-916.
Maruyama et al., FT-IR analysis of BSA fouled on ultrafiltration and microfiltration membranes, Journal of Membrane Science, 2001, vol. 192(1-2), pp. 201-207.
McDonald, et al., Selective Antibody Precipitation Using Polyelectrolytes: A Novel Approach to the Purification of Monoclonal Antibodies, A Novel Approach to the Purification of Monoclonal Antibodies, Biotechnology and Bioengineering, 2009, vol. 102(4), pp. 1141-1151.
Palacio et al., Application of a Pore-blockage-Cake-filtration Model to Protein Fouling During Microfiltration, Biotechnology and Bioengineering, 2002, vol. 79(3), pp. 260-270.
Rathore et al., Process analytical technology (PAT) for biopharmaceutical products, Analytical and Bioanalytical Chemistry, 2010, vol. 398(1), pp. 137-154.
Rathore et al., Large Scale Demonstration of a Process Analytical Technology Application in Bioprocessing: Use of On-line High Performance Liquid Chromatography for Making Real Time Pooling Decisions for Process Chromatography, Biotechnology Progress, 2010, vol. 26(2), pp. 448-457.
Rathore et al., Case Study and Application of Process Analytical Technology (PAT) Towards Bioprocessing: II. Use of Ultra-Performance Liquid Chromatography (UPLC) for Making Real-Time Pooling Decisions for Process Chromatography, Biotechnology and Bioengineering, 2008, vol. 101(6), pp. 1366-1374.
Roush et al., Advances in Primary Recovery: Centrifugation and Membrane Technology, Biotechnology Progress, 2008, vol. 24(3) pp. 488-495.
Saxena et al., Membrane-based techniques for the separation and purification of proteins: An overview, Advances in Colloid and Interface Science, 2009, vol. 145(1-2) pp. 1-22.
Taipa et al., Recovery of a monoclonal antibody from hybridoma culture supernatant by affinity precipitation with Eudragit S-100, Bioseparation, 2000, vol. 9(5), pp. 291-298.
Thommes et al., Alternatives to Chromatographic Separations, Biotechnology Progress, 2007, vol. 23(1), pp. 42-45.
Van Reis et al., Membrane separations in biotechnology, Current Opinion in Biotechnology, 2001, vol. 12(2), pp. 208-211.
Van Reis et al., Bioprocess membrane technology, Journal of Membrane Science, 2007, vol. 297(1-2), pp. 16-50.
Venkiteshwaran et al., Selective Precipitation-Assisted Recovery of Immunoglobulins From Bovine Serum Using Controlled-Fouling Crossflow Membrane Microfiltration, Biotechnology and Bioengineering, 2008, vol. 101(5) pp. 957-966.
Wisniewski et al., Floc size distribution in a membrane bioreactor and consequences for membrane fouling, Colloids and Surfaces a-Physicochemical and Engineering Aspects, 1998, vol. 138(2-3) pp. 403-411.
EP Supplementary European Search Report—dated Jun. 26, 2018.

* cited by examiner

PROCESS FOR PREPARING RECOMBINANT INSULIN USING MICROFILTRATION

CROSS REFERENCE TO RELATED APPLICATIONS

This application is the National Stage of International Application No. PCT/US2016/080534 filed on Mar. 3, 2016, which claims the benefit under 35 U.S.C. 119(e) of U.S. Provisional Application No. 62/130,690, filed Mar. 10, 2015.

BACKGROUND OF THE INVENTION (1) Field of the Invention

The present invention relates to the use of two tandem microfiltration (MF) steps in a process for making recombinant insulin.

(2) Description of Related Art

Tangential flow filtration (TFF) is a robust and versatile separation technique used in biopharmaceutical manufacturing. TFF is typically categorized as microfiltration (MF; pore sizing in microns) or ultrafiltration (UF; pore sizing in nominal molecular weight limit). MF processes have been classically employed in harvest and primary recovery, whereas UF processes have been largely used as polishing steps for buffer exchange or concentration (Marichal-Gallardo and Alvarez; van Reis and Zydney 2001).

Successful scale-up is a key challenge in implementation of microfiltration processes. Most commonly, MF unit operations are scaled on constant load factor (volume or mass per filter area), membrane channel geometry, path length, crossflow velocity, and transmembrane pressure (TMP) (Marichal-Gallardo and Alvarez 2012). However, performance upon scale-up is difficult to predict, heavily dependent on the nature of the feedstock, and often must be optimized empirically (Roush and Lu 2008; Saxena et al. 2009). The most common operational challenge for MF processes is filter fouling due to deposition of insoluble material on the membrane surface or inside membrane pores, which increases flow resistance (Marichal-Gallardo and Alvarez 2012; van Reis and Zydney 2007). Fouling is typically quantified as decreased flux at constant TMP or increased TMP at constant flux. Although models such as pore blockage, pore constriction, and cake filtration have been developed to aid in mitigation of fouling (Ho and Zydney 2000; Palacio et al. 2002), efficient scale-up remains a significant challenge.

BRIEF SUMMARY OF THE INVENTION

The present invention provides a process for producing proteins and peptides comprising two tandem microfiltration (MF) or diafiltration steps. The two MF steps comprise a single downstream purification step for purification of a protein or peptide, which may be performed subsequent to obtaining the protein or peptide from cell culture or in vitro synthesis to produce a purified or substantially purified protein or peptide product. The two MF steps may comprise a single upstream purification step in a process for producing a purified or substantially purified protein or peptide product that is performed before further downstream purification of the protein or peptide. The two MF steps facilitates purification of proteins and peptides by reducing both soluble and insoluble impurities that may be associated with the protein or peptide while providing for the exchange the protein or peptide into a suitable buffer for use or for downstream purification.

The process uses differential precipitation in combination with microfiltration to remove soluble and insoluble impurities from the protein or peptide. In one embodiment, in a first step, the protein or peptide is precipitated from soluble contaminants under conditions sufficient to precipitate the protein or peptide, e.g., adjusting the pH, salt concentration, or temperature of a solution comprising the protein or peptide to a pH, salt concentration, or temperature sufficient to precipitate the protein or peptide, and the soluble contaminants are removed from the precipitated protein or peptide by microfiltration. In a second step, the precipitated protein or peptide is solubilized under conditions sufficient to solubilize the protein or peptide, e.g., adjusting the pH, salt concentration, or temperature of a solution comprising the precipitated protein or peptide to a pH, salt concentration, or temperature sufficient to solubilize the protein or peptide, and the insoluble contaminants are removed from the solubilized protein or peptide by microfiltration.

The present invention provides, a process for producing a protein or peptide comprising two tandem microfiltration steps to produce the insulin or insulin analog.

In particular aspects, the two tandem microfiltration steps include a first microfiltration step in which soluble impurities are removed and a second microfiltration step in which insoluble impurities are removed.

In particular aspects, the two tandem microfiltration steps are performed downstream from a step in which the protein or peptide is obtained from a cell culture and upstream from a chromatography step for purifying the protein or peptide.

In particular aspects, in the first microfiltration step the protein or peptide is precipitated from a first aqueous solution and retained by a microfilter and soluble impurities are permeated through the microfilter and in the second microfiltration step the protein or peptide retained by the microfilter is solubilized into a second aqueous solution and the solubilized protein or peptide is permeated through the microfilter.

In particular aspects, the protein or peptide is precipitated from the first aqueous solution by adjusting the pH of the first aqueous solution to a pH sufficient to precipitate the protein or peptide and the precipitated protein or peptide is solubilized in the second aqueous solution by adjusting the pH of the second aqueous solution to a pH sufficient to solubilize the protein or peptide.

The present invention further provides a process for producing a protein or peptide, comprising (a) providing an aqueous solution of the protein or peptide comprising a mixture of the protein and process-related impurities; (b) adjusting the pH of the aqueous solution to a pH sufficient to effect precipitation of the protein or peptide from the aqueous solution to provide an aqueous mixture comprising precipitated protein or peptide and soluble and precipitated impurities; (c) applying the aqueous mixture to a surface of a microfilter having an exclusion pore size sufficient to retain the precipitated protein or peptide; (d) permeating the aqueous mixture through the microfilter to remove the soluble impurities from the precipitated protein or peptide retained by the microfilter and washing the precipitated protein or peptide retained by the microfilter with water or a first aqueous solution at a pH that is at or within 1.5 pH unit of the pH of the pH-adjusted aqueous mixture; (e) adding a second aqueous solution to the precipitated protein or peptide retained by the microfilter and adjusting the pH to a pH sufficient to solubilize the precipitated protein or peptide;

and (f) permeating the second aqueous solution comprising the solubilized protein or peptide through the microfilter and collecting a permeate pool comprising the protein or peptide to produce the protein or peptide.

The present invention further provides a process for producing a protein or peptide, comprising (a) providing an aqueous solution of the protein or peptide; (b) adjusting the pH of the aqueous solution to a pH sufficient to precipitate the protein or peptide from the aqueous solution to provide an aqueous mixture of precipitated protein or peptide and soluble and precipitated impurities; (c) applying the aqueous mixture to a surface of a microfilter having a pore exclusion size sufficient to retain the precipitated protein or peptide thereto to provide a first retentate pool and permeating the soluble impurities that are smaller than the exclusion pore size of the microfilter through the microfilter by washing the retentate pool with water or a first aqueous solution at a pH that is at or within 1.5 pH units of the pH of the pH-adjusted aqueous mixture for a time sufficient to substantially remove the soluble impurities from the first retentate pool to provide a second retentate pool; and (d) adjusting the pH of the second retentate pool to a pH sufficient to solubilize the precipitated protein or peptide to provide a third retentate pool and permeating the third retentate pool comprising the solubilized protein or peptide through the microfilter wherein insoluble impurities and impurities that are larger than the exclusion pore size of the microfilter are retained by the microfilter and collecting a permeate pool comprising the insulin or insulin analog to produce the protein or peptide.

The present invention further provides a process for producing a protein or peptide, comprising (a) providing an aqueous solution of the protein or peptide; (b) adjusting the pH of the aqueous solution to a pH sufficient to effect precipitation of the protein or peptide from the aqueous solution to provide an aqueous mixture containing precipitated protein or peptide and soluble and precipitated impurities; (c) applying the aqueous mixture to a surface of a microfilter having an exclusion pore size sufficient to retain the precipitated protein or peptide thereto to provide a first retentate pool; (d) permeating the first retentate pool through the microfilter to remove the soluble impurities from the precipitated protein or peptide retained by the microfilter while adding water or a first aqueous solution at a first pH that is at or within 1.5 pH unit of the pH of the pH-adjusted aqueous mixture to the retentate pool at a rate that is substantially the same as the rate the first retentate pool is permeating through the microfilter and for a time sufficient to substantially reduce the amount of the soluble impurities in the first retentate pool to provide a second retentate pool; (e) adding a second aqueous solution to the second retentate pool and adjusting the pH to a second pH sufficient to solubilize the precipitated protein or peptide and to provide a third retentate pool; and (f) permeating the third retentate pool through the microfilter for a time sufficient to reduce the volume of the third retentate pool to produce a reduced-volume third retentate pool while collecting the permeate comprising the solubilized protein or peptide to provide a permeate pool; and (g) permeating the reduced-volume third retentate pool through the microfilter into the permeate pool while adding a third aqueous solution at a pH that is at or within 1.5 pH unit of the second pH to the reduced-volume third retentate pool at a rate that is substantially the same as the rate the reduced-volume third retentate pool is permeating through the microfilter for a time sufficient to substantially recover the solubilized protein or peptide in the reduced-volume third retentate pool; wherein the permeate pool provides the protein or peptide.

The present invention further provides a process for producing a protein or peptide, comprising (a) providing an aqueous solution of the protein or peptide; (b) adjusting the pH of the aqueous solution to a pH sufficient to effect precipitation of the protein or peptide from the aqueous solution to provide an aqueous mixture containing precipitated protein or peptide and soluble and precipitated impurities; (c) applying the aqueous mixture to a surface of a microfilter having an exclusion pore size sufficient to retain the precipitated protein or peptide thereto to provide a first retentate pool; (d) sequentially diluting the first retentate pool with a predetermined volume of water or a first aqueous solution at a first pH that is at or within 1.5 pH unit of the pH of the pH-adjusted aqueous mixture and permeating the diluted first retentate pool through the microfilter to remove the soluble impurities from the precipitated protein or peptide retained by the microfilter for a number of cycles sufficient to substantially reduce the amount of the soluble impurities in the first retentate pool to provide a second retentate pool; (e) adding a second aqueous solution to the second retentate pool and adjusting the pH to a second pH sufficient to solubilize the precipitated protein or peptide and to provide a third retentate pool; and (f) permeating the third retentate pool through the microfilter for a time sufficient to reduce the volume of the third retentate pool to produce a reduced-volume third retentate pool while collecting the permeate comprising the solubilized protein or peptide to provide a permeate pool; and (g) sequentially diluting the reduced-volume third retentate pool with a predetermined volume of a third aqueous solution at a pH that is at or within 1.5 pH unit of the second pH to the reduced-volume third retentate pool and permeating the reduced-volume third retentate pool through the microfilter into the permeate pool for a number of cycles sufficient to substantially recover the solubilized protein or peptide in the reduced-volume third retentate pool; wherein the permeate pool provides the protein or peptide.

In a further aspect, sequentially diluting the first retentate pool with one first retentate volume of water or a first aqueous solution at a first pH that is at or within 1.5 pH unit of the pH of the pH-adjusted aqueous mixture and permeating the diluted first retentate pool through the microfilter to remove the soluble impurities from the precipitated protein or peptide retained by the microfilter for at least one, two, three, or four cycles to provide the second retentate pool.

In a further aspect, diluting the third retentate pool volume up to 2 fold with a third aqueous solution at a pH that is at or within 1.5 pH unit of the second pH to third retentate pool and then reducing the diluted third retentate pool by permeating the diluted third retentate pool through the microfilter into the permeate pool. The reduced-volume third permeate pool is then diafiltered for at least one, two, three, four, five, or six cycles recover the solubilized insulin or insulin analog in the reduced-volume third retentate pool.

In a further aspect, sequentially diluting the reduced-volume third retentate pool with one reduced-volume third retentate volume of a third aqueous solution at a pH that is at or within 1.5 pH unit of the second pH to the reduced-volume third retentate pool and permeating the reduced-volume third retentate pool through the microfilter into the permeate pool for at least one, two, three, four, five, or six cycles recover the solubilized protein or polypeptide in the reduced-volume third retentate pool.

In particular aspects of the above embodiments, the microfilter is a tangential flow flat sheet or hollow fiber microfilter.

In particular aspects of the above embodiments, the pore exclusion size is sufficient to permit the passage of solubilized recombinant insulin or insulin analog through the microfilter.

In particular aspects of the above embodiments, the microfilter has a membrane pore size of about 0.1 μm.

In particular aspects of the above embodiments, performance of the tandem microfiltration step is monitored using ultraviolet absorbance, high performance liquid chromatography (HPLC), or ultra-high performance chromatography (UHPLC).

The present invention further provides a process for producing insulin or insulin analogs (insulin product) comprising two tandem microfiltration (MF) or diafiltration steps. The two MF steps comprise a single downstream purification step that follows enzymatic digestion pre-proinsulin or insulin analog to make insulin or insulin analog and is before further downstream purification such as chromatography. The two MF steps facilitates purification of the insulin or insulin analog by reducing both soluble and insoluble impurities that may be associated with the insulin or insulin analog following enzymatic digestion while providing for the exchange the insulin or insulin analog into a suitable buffer for downstream purification.

The present invention provides, a process for producing insulin or insulin analog comprising two tandem microfiltration steps to produce the insulin or insulin analog.

In particular aspects, the two tandem microfiltration steps include a first microfiltration step in which soluble impurities are removed and a second microfiltration step in which insoluble impurities are removed.

In particular aspects, the two tandem microfiltration steps are performed downstream from an enzymatic digestion step in which pre-proinsulin or pre-proinsulin analog is digested to produce insulin or insulin analog and upstream from a chromatography step for purifying the insulin or insulin analog.

In particular aspects, in the first microfiltration step the insulin or insulin analog is precipitated from a first aqueous solution and retained by a microfilter and soluble impurities are permeated through the microfilter and in the second microfiltration step the insulin or insulin analog retained by the microfilter is solubilized into a second aqueous solution and the solubilized insulin or insulin analog is permeated through the microfilter.

In particular aspects, the precipitation of the insulin or insulin analog in the first microfiltration step may be achieved by using zinc, for example, zinc oxide or zinc chloride and the solubilization in the second step may be achieved by adjusting the pH of the second aqueous solution to a pH sufficient to solubilize the insulin or insulin analog.

In particular aspects, the insulin or insulin analog is precipitated from the first aqueous solution by adjusting the pH of the first aqueous solution to a pH sufficient to precipitate the insulin or insulin analog and the precipitated insulin or insulin analog is solubilized in the second aqueous solution by adjusting the pH of the second aqueous solution to a pH sufficient to solubilize the insulin or insulin analog.

In particular aspects, the first aqueous solution comprises a first buffering agent and the second aqueous solution comprises water or a second buffering agent. In further aspects, the buffering agent comprises an organic acid, its salt form, or both the organic acid and its salt form.

In particular aspects, the first buffering agent comprises citric acid and the second buffering agent comprises acetic acid.

In particular aspects, the first buffering agent and the second buffering agent are both acetic acid.

In particular aspects, the microfilter is a tangential flow flat sheet or hollow fiber microfilter.

In particular aspects, the pore exclusion size is sufficient to permit the passage of solubilized recombinant insulin or insulin analog through the microfilter.

In particular aspects, the microfilter has a membrane pore size of about 0.1 μm.

In particular aspects, the insulin is native human, porcine, or bovine insulin.

In particular aspects, the insulin analog is an acid-stable insulin analog or a pI-shifted insulin analog in which the pI of the insulin analog is less than or greater than the pI of native human insulin.

In particular aspects, the insulin analog is insulin glargine, insulin aspart, insulin glulisine, or insulin lispro.

In particular aspects, performance of the tandem microfiltration step is monitored using ultraviolet absorbance, high performance liquid chromatography (HPLC), or ultra-high performance chromatography (UHPLC).

The present invention further provides a process for producing insulin or insulin analog, comprising (a) providing an aqueous solution of enzymatically digested recombinant pre-proinsulin or pre-proinsulin analog comprising a mixture of insulin or insulin analog, digest related impurities and host-cell impurities; (b) adjusting the pH of the aqueous solution to a pH sufficient to effect precipitation of the insulin or insulin analog from the aqueous solution to provide an aqueous mixture comprising precipitated insulin or insulin analog and soluble and precipitated digest related impurities and host-cell impurities; (c) applying the aqueous mixture to a surface of a microfilter having an exclusion pore size sufficient to retain the precipitated insulin or insulin analog thereto; (d) permeating the aqueous mixture through the microfilter to remove the soluble impurities from the precipitated insulin or insulin analog retained by the microfilter and washing the precipitated recombinant insulin or insulin analog retained by the microfilter with water or a first aqueous solution at a pH that is at or within 1.5 pH unit of the pH of the pH-adjusted aqueous mixture; (e) adding a second aqueous solution to the precipitated insulin or insulin analog retained by the microfilter and adjusting the pH to a pH sufficient to solubilize the precipitated insulin or insulin analog; and (f) permeating the second aqueous solution comprising the solubilized recombinant insulin or insulin analog through the microfilter and collecting a permeate pool comprising the insulin or insulin analog to produce the insulin or insulin analog.

The present invention provides a process for producing insulin or insulin analog, comprising (a) providing an aqueous solution of enzymatically digested pre-proinsulin comprising a mixture of insulin or insulin analog, digest related impurities and host-cell impurities; (b) adjusting the pH of the aqueous solution to a pH sufficient to precipitate the insulin or insulin analog from the aqueous solution to provide an aqueous mixture of precipitated insulin or insulin analog and soluble and precipitated digest related impurities and host-cell impurities; (c) applying the aqueous mixture to a surface of a microfilter having a pore exclusion size sufficient to retain the precipitated insulin or insulin analog thereto to provide a first retentate pool and permeating the soluble impurities that are smaller than the exclusion pore size of the microfilter through the microfilter by washing the retentate pool with water or a first aqueous solution at a pH that is at or within 1.5 pH units of the pH of the pH-adjusted aqueous mixture for a time sufficient to substantially remove the soluble impurities from the first retentate pool to provide a second retentate pool; and (d) adjusting the pH of the second retentate pool to a pH sufficient to solubilize the precipitated insulin or insulin analog to provide a third retentate pool and permeating the third retentate pool comprising the solubilized insulin or insulin analog through the microfilter wherein insoluble impurities and impurities that are larger than the exclusion pore size of the microfilter are retained by the microfilter and collecting a permeate pool comprising the insulin or insulin analog to produce the insulin or insulin analog.

The present invention provides a process for producing insulin or insulin analog, comprising (a) providing an aqueous solution of enzymatically digested pre-proinsulin or pre-proinsulin analog comprising a mixture of insulin or insulin analog, digest related impurities and host-cell impurities; (b) adjusting the pH of the aqueous solution to a pH sufficient to effect precipitation of the insulin or insulin analog from the aqueous solution to provide an aqueous mixture containing precipitated insulin or insulin analog and soluble and precipitated digest related impurities and host-cell impurities; (c) applying the aqueous mixture to a surface of a microfilter having an exclusion pore size sufficient to retain the precipitated insulin or insulin analog to provide a first retentate pool; (d) permeating the first retentate pool through the microfilter to remove the soluble digest related impurities and host-cell impurities from the precipitated insulin or insulin analog retained by the microfilter while adding water or a first aqueous solution at a first pH that is at or within 1.5 pH unit of the pH of the pH-adjusted aqueous mixture to the retentate pool at a rate that is substantially the same as the rate the first retentate pool is permeating through the microfilter and for a time sufficient to substantially reduce the amount of the soluble digest related impurities and host-cell impurities in the first retentate pool to provide a second retentate pool; (e) adding a second aqueous solution to the second retentate pool and adjusting the pH to a second pH sufficient to solubilize the precipitated insulin or insulin analog and to provide a third retentate pool; and (f) permeating the third retentate pool through the microfilter for a time sufficient to reduce the volume of the third retentate pool to produce a reduced-volume third retentate pool while collecting the permeate comprising the solubilized insulin or insulin analog to provide a permeate pool; and (g) permeating the reduced-volume third retentate pool through the microfilter into the permeate pool while washing with a third aqueous solution at a pH that is at or within 1.5 pH unit of the second pH to the reduced-volume third retentate pool at a rate that is substantially the same as the rate the reduced-volume third retentate pool is permeating through the microfilter for a time sufficient to substantially recover the solubilized insulin or insulin analog in the reduced-volume third retentate pool; wherein the permeate pool provides the insulin or insulin analog.

In a further aspect, the first retentate pool is washed with at least one, two, three, or four first retentate pool volumes of the water or first aqueous solution.

In a further aspect, the reduced-volume third retentate pool is washed with at least one, two, three, four, five, or six reduced-volume third retentate pool volumes of the third aqueous solution at a pH that is at or within 1.5 pH unit of the second pH.

The present invention provides a process for producing insulin or insulin analog, comprising (a) providing an aqueous solution of enzymatically digested pre-proinsulin or pre-proinsulin analog comprising a mixture of insulin or insulin analog, digest related impurities and host-cell impurities; (b) adjusting the pH of the aqueous solution to a pH sufficient to effect precipitation of the insulin or insulin analog from the aqueous solution to provide an aqueous mixture containing precipitated insulin or insulin analog and soluble and precipitated digest related impurities and host-cell impurities; (c) applying the aqueous mixture to a surface of a microfilter having an exclusion pore size sufficient to retain the precipitated insulin or insulin analog thereto to provide a first retentate pool; (d) sequentially diluting the first retentate pool with a predetermined volume of water or a first aqueous solution at a first pH that is at or within 1.5 pH unit of the pH of the pH-adjusted aqueous mixture and permeating the diluted first retentate pool through the microfilter to remove the soluble digest related impurities and host-cell impurities from the precipitated insulin or insulin analog retained by the microfilter for a number of cycles sufficient to substantially reduce the amount of the soluble digest related impurities and host-cell impurities in the first retentate pool to provide a second retentate pool; (e) adding a second aqueous solution to the second retentate pool and adjusting the pH to a second pH sufficient to solubilize the precipitated insulin or insulin analog and to provide a third retentate pool; and (f) permeating the third retentate pool through the microfilter for a time sufficient to reduce the volume of the third retentate pool to produce a reduced-volume third retentate pool while collecting the permeate comprising the solubilized insulin or insulin analog to provide a permeate pool; and (g) sequentially diluting the reduced-volume third retentate pool with a predetermined volume of a third aqueous solution at a pH that is at or within 1.5 pH unit of the second pH to the reduced-volume third retentate pool and permeating the reduced-volume third retentate pool through the microfilter into the permeate pool for a number of cycles sufficient to substantially recover the solubilized insulin or insulin analog in the reduced-volume third retentate pool; wherein the permeate pool provides the insulin or insulin analog.

In a particular aspect, the sequentially diluting the first retentate pool with one first retentate volume of water or a first aqueous solution at a first pH that is at or within 1.5 pH unit of the pH of the pH-adjusted aqueous mixture and permeating the diluted first retentate pool through the microfilter to remove the soluble digest related impurities and host-cell impurities from the precipitated insulin or insulin analog on the surface of the microfilter for at least one, two, three, or four cycles to provide the second retentate pool.

wherein diluting the third retentate pool volume up to 2 fold with a third aqueous solution at a pH that is at or within 1.5 pH unit of the second pH to third retentate pool and then reducing the diluted third retentate pool by permeating the diluted third retentate pool through the microfilter into the permeate pool. The reduced-volume third permeate pool is then diafiltered for at least one, two, three, four, five, or six cycles recover the solubilized insulin or insulin analog in the reduced-volume third retentate pool.

In a particular aspect, the sequentially diluting the reduced-volume third retentate pool with one reduced-volume third retentate volume of a third aqueous solution at a pH that is at or within 1.5 pH unit of the second pH to the reduced-volume third retentate pool and permeating the reduced-volume third retentate pool through the microfilter into the permeate pool for at least one, two, three, four, five, or six cycles recover the solubilized insulin or insulin analog in the reduced-volume third retentate pool.

In particular aspects of any one of the aforementioned embodiments, the microfilter is a tangential flow microfilter. The microfilter in anyone of the above mentioned embodiments has a pore exclusion size sufficient to retain the precipitated recombinant insulin thereto but which is sufficient to permit the passage of solubilized recombinant insulin or insulin analog through the microfilter, for example, a microfilter having a membrane pore size of about 0.1 µm.

In further aspects of the above embodiments, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6 thus a pI shifted insulin analog has a pI greater than 5.6 or less than 5.4. In particular aspects the insulin analog has a pI from between 5.8 to 8.0. An acid-stable insulin analog such as insulin glargine has a pI of about 6.7 to 7.36. In a further aspect, the insulin analog is insulin glargine, insulin aspart, insulin glulisine, or insulin lispro.

In particular aspects, the first aqueous solution comprises a first buffering agent and the second aqueous solution comprises water or a second buffering agent. In further aspects, the buffering agent comprises an organic acid, its salt form, or both the organic acid and its salt form. In further aspects, the organic acid is acetic acid and/or citric acid. Thus, in particular aspects, the first aqueous solution comprises citric acid and the second aqueous solution comprises acetic acid or the first aqueous solution comprises acetic acid and the second aqueous solution comprises acetic acid. In further aspects, the organic acid salt is acetate and/or citrate. Thus, in particular aspects, the first aqueous solution comprises citric acid and/or citrate and the second aqueous solution comprises acetic acid and/or acetate or the first aqueous solution comprises acetic acid and/or acetate and the second aqueous solution comprises acetic acid and/or acetate.

In further aspects of the above embodiments, the first and second aqueous solutions comprise acetic acid or the first aqueous solution comprises citric acid and the second aqueous solution comprises acetic acid.

In a further aspect, the performance of the process is monitored using ultraviolet absorbance, high performance liquid chromatography (HPLC), or ultra-high performance chromatography (UHPLC).

In a further aspect, the first retentate pool is washed with at least one, two, three, or four first retentate pool volumes of the water or first aqueous solution.

In a further aspect, at least one, two, three, four, five, or six reduced-volume third retentate pool volumes of the third aqueous solution at a pH that is at or within 1.5 pH unit of the second pH is added to the third retentate pool.

In a further embodiment, the present invention provides a process for producing insulin or insulin analog, wherein the process has a digestion step in which pre-proinsulin or pre-proinsulin analog is digested with one or more proteolytic enzymes to produce an aqueous solution of insulin or insulin analog, digestion byproducts, and host cell impurities and a downstream purification or chromatography step, in which the insulin or insulin analog is separated from the digestion byproducts, and host cell impurities, wherein the improvement comprises performing two tandem microfiltration steps subsequent to the digestion step and prior to the downstream purification or chromatography step.

In a further aspect, the microfiltration step comprises (a) adjusting the pH of the aqueous solution from the digestion step to a pH sufficient to precipitate the insulin or insulin analog from the aqueous solution to provide an aqueous mixture comprising precipitated insulin or insulin analog and soluble and precipitated digest related impurities and host-cell impurities; (b) applying the aqueous mixture to a surface of a microfilter having a pore exclusion size sufficient to retain the precipitated insulin or insulin analog thereto to provide a first retentate pool; (c) permeating the soluble impurities that are smaller than the exclusion pore size of the microfilter through the microfilter while washing the first retentate pool with water or a first aqueous solution at a pH that is at or within 1.5 pH units of the pH of the pH-adjusted aqueous mixture for a time sufficient to substantially remove the soluble impurities from the first retentate pool to provide a second retentate pool; and (d) adding a second aqueous solution to the second retentate pool and adjusting the pH of the third retentate pool to a pH sufficient to solubilize the precipitated insulin or insulin analog to provide a third retentate pool and permeating the third retentate pool containing the solubilized insulin or insulin analog through the microfilter wherein insoluble impurities and impurities larger than the exclusion pore size of the microfilter are retained by the microfilter and a permeate pool comprising the solubilized insulin or insulin analog is collected to produce the insulin or insulin analog.

In particular aspects of the aforementioned improvements, the microfilter is a tangential flow microfilter. The microfilter in anyone of the above mentioned embodiments has a pore exclusion size sufficient to retain the precipitated recombinant insulin thereto but which is sufficient to permit the passage of solubilized recombinant insulin or insulin analog through the microfilter, for example, a microfilter having a membrane pore size of about 0.1 µm.

In further aspects of the above improvements, the insulin is native human, porcine, or bovine insulin. In further aspects, the insulin analog is an acid-stable insulin analog, which is stable and soluble in acidic or weakly acidic solutions and insoluble or partially insoluble at physiological pH, or a pI-shifted insulin analog in which the pI of the insulin analog is less than or greater than the pI of native human insulin. The pI of native insulin is 5.4 to 5.6 thus a pI shifted insulin analog has a pI greater than 5.6 or less than 5.4. In particular aspects the insulin analog has a pI from between 5.8 to 8.0. An acid-stable insulin analog such as insulin glargine has a pI of about 6.7 to 7.0. In a further aspect, the insulin analog is insulin glargine, insulin aspart, insulin glulisine, or insulin lispro.

In further aspects of the above improvements, the first and second aqueous mixtures comprise acetic acid or the first aqueous solution comprises citric acid and the second aqueous solution comprises acetic acid.

In particular aspects of the above improvements the downstream purification or chromatography step comprises anion exchange chromatography, cation exchange chromatography or mixed mode anion exchange chromatography, reverse phase high pressure liquid chromatography (RP-HPLC), or hydrophobic interaction chromatography (HIC).

In a further aspect, the performance of the tandem microfiltration step is monitored using ultraviolet absorbance, high performance liquid chromatography (HPLC), or ultra-high performance chromatography (UHPLC).

Definitions

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "insulin analog" as used herein includes any heterodimer analog that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; and/or deleting any or all of positions B1-4 and B26-30. Insulin analogs include molecules having one to 10 amino acids at the N or C terminus of the A-chain peptide and/or B-chain peptide. Insulin analogs further include molecules amidated at the C-terminus of the A-chain peptide and/or B-chain peptide. Examples of insulin analogs include but are not limited to the insulin analogs disclosed in published international application WO20100080606, WO2009/099763, and WO2010080609, the disclosures of which are incorporated herein by reference. Insulin glargine (Gly(A21), Arg(B31), Arg(B32)-human insulin: A-chain peptide SEQ ID NO:3; B-chain peptide SEQ ID NO:4), insulin lispro (Lys(B28), Pro(B29)-human insulin: A-chain peptide SEQ ID NO:1; B-chain peptide SEQ ID NO:5, insulin glusiline (Lys(B3), Glu(B29)-human insulin: A-chain peptide SEQ ID NO:1; B-chain peptide SEQ ID NO:6), insulin detemir (Lys-myristic acid(B29)-human insulin: A-chain peptide SEQ ID NO:1; B-chain peptide SEQ ID NO:2 with B-29 acylated with myristic acid), insulin aspart (Asp(B28)-human insulin: A-chain peptide SEQ ID NO:1; B-chain peptide SEQ ID NO:7) are examples of commercially available insulin analogs.

The term "insulin analogs" further includes heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analog is a partial agonist that has from 2× to 100× less activity at the insulin receptor as does native insulin. In other aspects, the insulin analog has enhanced activity at the insulin receptor. In other aspects, the insulin analog has enhanced activity at the insulin receptor, for example, the IGF$^{B16B17}$ derivative peptides disclosed in published international application WO2010080607 (which is incorporated herein by reference). These insulin analogs, which have reduced activity at the insulin growth hormone receptor and enhanced activity at the insulin receptor, include both heterodimers and single-chain analogs.

The term "properly folded" refers to insulin or insulin analogs in which the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

As used herein, the term "single-chain insulin" or "single-chain insulin analog" encompasses a group of structurally-related proteins wherein the A-chain peptide or functional analog and the B-chain peptide or functional analog are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analog further includes three disulfide bonds: the first disulfide bond is between the cysteine residues at positions 6 and 11 of the A-chain or functional analog thereof, the second disulfide bond is between the cysteine residues at position 7 of the A-chain or functional analog thereof and position 7 of the B-chain or functional analog thereof, and the third disulfide bond is between the cysteine residues at position 20 of the A-chain or functional analog thereof and position 19 of the B-chain or functional analog thereof.

As used herein, the term "connecting peptide" or "C-peptide" refers to the connection moiety "C" of the B-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide, the monkey C-peptide, and any other peptide from 3 to 35 amino acids that connects the B-chain to the A-chain thus is meant to encompass any peptide linking the B-chain peptide to the A-chain peptide in a single-chain insulin analog (See for example, U.S. Published application Nos. 20090170750 and 20080057004 and WO9634882) and in insulin precursor molecules such as disclosed in WO9516708 and U.S. Pat. No. 7,105,314.

As used herein, the term "pre-proinsulin" refers to a fusion protein comprising a leader peptide, which targets the pre-proinsulin analog precursor to the secretory pathway of the host cell, fused to the N-terminus of a B-chain peptide or B-chain peptide analog, which is fused to the N-terminus of a C-peptide which in turn is fused at its C-terminus to the N-terminus of an A-chain peptide or A-chain peptide analog. The fusion protein may optionally include one or more extension or spacer peptides between the C-terminus of the leader peptide and the N-terminus of the B-chain peptide or B-chain peptide analog. The extension or spacer peptide when present may protect the N-terminus of the B-chain or B-chain analog from protease digestion during fermentation.

As used herein, the term "proinsulin" refers to a molecule in which the signal or pre-peptide of the pre-proinsulin analog precursor has been removed.

As used herein, the term "leader peptide" refers to a polypeptide comprising a pre-peptide (the signal peptide) and a propeptide.

As used herein, the term "signal peptide" refers to a pre-peptide which is present as an N-terminal peptide on a precursor form of a protein. The function of the signal peptide is to facilitate translocation of the expressed polypeptide to which it is attached into the endoplasmic reticulum. The signal peptide is normally cleaved off in the course of this process. The signal peptide may be heterologous or homologous to the organism used to produce the polypeptide. A number of signal peptides which may be used include the yeast aspartic protease 3 (YAP3) signal peptide or any functional analog (Egel-Mitani et al. YEAST 6:127 137 (1990) and U.S. Pat. No. 5,726,038) and the signal peptide of the *Saccharomyces cerevisiae* mating factor al gene (ScMF α1) gene (Thorner (1981) in The Molecular Biology of the Yeast *Saccharomyces cerevisiae*, Strathern et al., eds., pp 143 180, Cold Spring Harbor Laboratory, NY and U.S. Pat. No. 4,870,008.

As used herein, the term "propeptide" refers to a peptide whose function is to allow the expressed polypeptide to which it is attached to be directed from the endoplasmic reticulum to the Golgi apparatus and further to a secretory vesicle for secretion into the culture medium (i.e., exportation of the polypeptide across the cell wall or at least through the cellular membrane into the periplasmic space of the yeast cell). The propeptide may be the ScMF α1 (See U.S. Pat. Nos. 4,546,082 and 4,870,008). Alternatively, the propeptide may be a synthetic propeptide, which is to say a propeptide not found in nature, including but not limited to those disclosed in U.S. Pat. Nos. 5,395,922; 5,795,746; and 5,162,498 and in WO 9832867. The propeptide will preferably contain an endopeptidase processing site at the C-terminal end, such as a Lys-Arg sequence or any functional analog thereof.

The term "pharmaceutically pure" refers to an insulin or insulin analog that is greater than 99 percent pure with respect to contaminating macromolecules, particularly other proteins and nucleic acids, and free of infectious and pyrogenic agents.

The term "diafiltration" refers to a technique that uses microfiltration membranes to completely remove or lower the concentration of salt or solvent, or to replace buffer salts from solutions containing proteins and other large molecules.

The term "diafiltration volume" refers to the initial volume in which the molecule of interest is suspended. The number of diafiltration volumes required depends on whether the permeating species is freely passing (salts, buffers, solvents) or partially retained by the microfiltration membrane.

The term "continuous diafiltration" refers to the technique of continuous diafiltration (also referred to as constant volume diafiltration) wherein washing out the original buffer salts (or other low molecular weight or soluble species) in the retentate pool (sample) by adding water or a buffer to the retentate pool at the same rate as filtrate is being generated.

The term "discontinuous diafiltration-sequential dilution" refers sequential dilution wherein the sample is first diluted to a predetermined volume, then concentrated back to its original volume with water or replacement buffer. This is repeated until the unwanted salts, solvents, or smaller molecules or soluble species are removed. Each subsequent dilution removes more of the unwanted salts, solvents, or smaller molecules or soluble species.

The term "permeating" refers to the process of transferring substances from one side of a microfilter membrane to the other side.

The term "retentate pool" refers to the material that is retained on the one side of the microfilter.

The term "permeate" refers to the material that passes through the microfilter.

The term "tangential flow filtration" or "crossflow filtration" refers to a filtration process in which the bulk solution flows over and parallel to the filter surface, and under pressure, such that a portion of the solvent is forced through the membrane filter.

BRIEF DESCRIPTION OF THE DRAWINGS

FIG. 1A: In MF1, precipitated product is diafiltered and soluble impurities are removed in the permeate stream. FIG. 1B: In MF2, purified product is resolubilized and recovered in the permeate stream via diafiltration, while insoluble impurities remain in the retentate pool.

DETAILED DESCRIPTION OF THE INVENTION

Figure 1A:
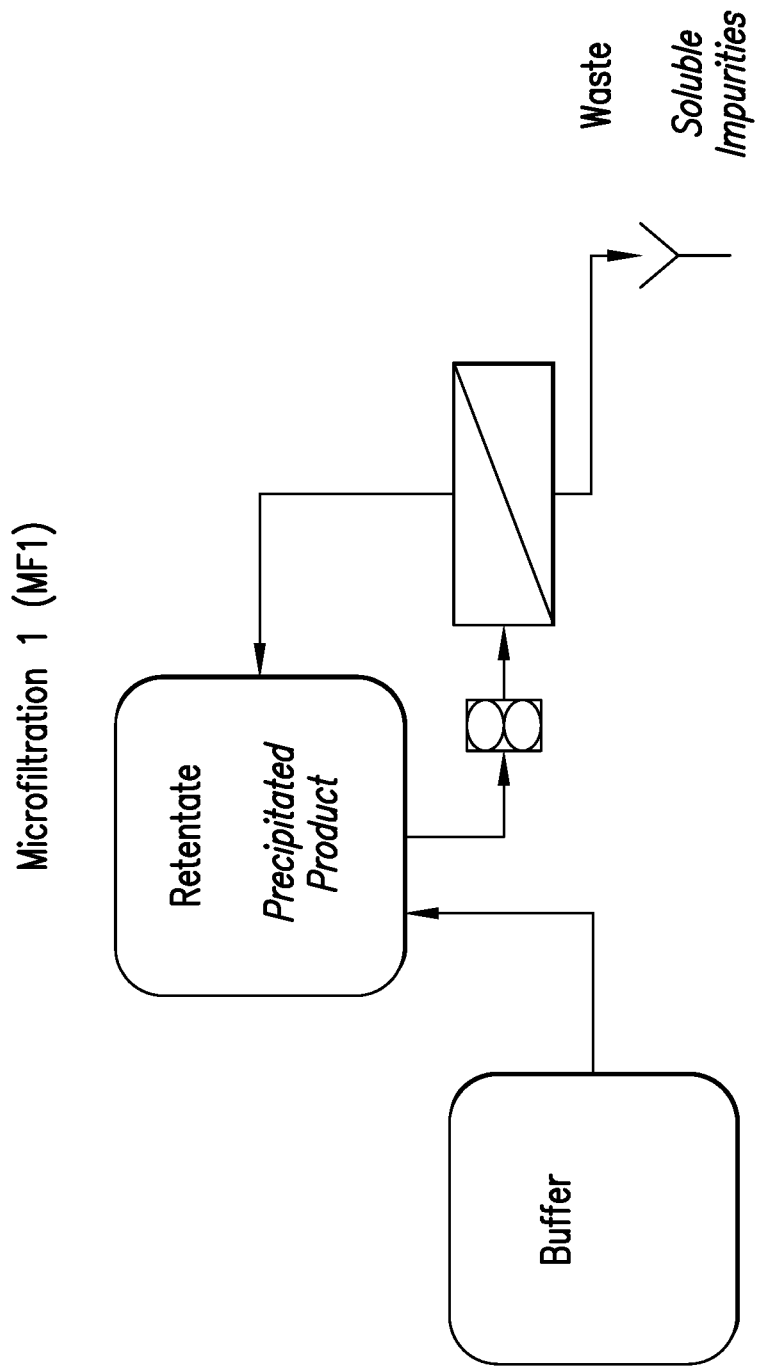
FIG. 1A and FIG. 1B. Microfiltration unit operations in the downstream purification of a recombinant protein.

Microfiltration (or diafiltration) processes have been classically employed in harvest and primary recovery unit operations, but are not typically used in downstream purification. In contrast, ultrafiltration (UF) processes have been largely used as polishing steps for buffer exchange or concentration. The present invention provides in a process for producing recombinant insulin the application of MF for downstream impurity purification and more specifically use of two tandem MF steps for sequential clearance of both soluble and insoluble impurities.

Microfiltration has been proposed as a downstream purification step in tandem with selective precipitation of either product or undesired impurities (Ge et al. 2006; Venkiteshwaran et al. 2008). Selective precipitation can be achieved through pH, heat, salt, or affinity interaction (Bentham et al. 1988; Bramaud et al. 1997; McDonald et al. 2009; Taipa et al. 2000), and microfiltration is a cost-effective alternative to centrifugation for separation of soluble from insoluble material has been evaluated inter alia as an alternative to Protein A capture for monoclonal antibody purification (Gagnon 2012; Thommes and Etzel 2007).

The unique, differentiating aspect of the present invention is the use of two tandem microfiltration (MF) steps in a single downstream purification unit operation that functions to reduce both soluble and insoluble impurities from recombinant proteins or peptides and to exchange the recombinant proteins or peptides into a suitable buffer for downstream purification. In the first microfiltration step (MF1), the recombinant protein or peptide is precipitated. This allows for its separation from soluble impurities such as host DNA, host cell protein (HCP), upstream process impurities or by-products (e.g., cleaved C-peptide and N-terminal fusion) and residual enzymes via diafiltration during the microfiltration stage of the operation. The precipitated recombinant protein or peptide is then concentrated and washed via diafiltration to reduce the amount of soluble impurities; the recombinant protein or peptide remains as a precipitate on the retentate side of the membrane. In the second microfiltration step (MF2), the recombinant protein or peptide is resolubilized and recovered in the permeate stream. Insoluble impurities are retained by the membrane, then concentrated and discarded with the retentate pool at the end of the step.

However, microfiltration has not been proposed as a step in the process of purifying insulin.

Typically, insulin is produced recombinantly as a pre-proinsulin in either *E. coli* or in yeast such as *S. cerevisiae*. The production of recombinant insulin or insulin analogs requires an enzymatic digest step to cleave the leader sequence and C-peptide of the pre-proinsulin molecule to form the desired, active insulin molecule. The digest results in additional impurities that must be removed from the process in order to produce a sufficiently pure insulin or insulin analog. These impurities include the cleaved leader sequence, the C-peptide, any miscleaved pre-proinsulin that occurred during digestion as well as the enzyme(s) used for digestion. Following enzymatic digestion of the pre-proinsulin to produce insulin, the insulin purified from enzymatic digestion impurities and/or host cell impurities by one or more downstream purification or chromatography steps. In some cases, the insulin may be precipitated from soluble impurities prior to the one or more downstream purification or chromatography steps. The present invention provides an improvement to the typical process for producing insulin by providing the two tandem microfiltration steps subsequent to the enzymatic digestion and prior to the downstream purification or chromatography steps to remove impurities that are soluble under conditions when the insulin is rendered insoluble and remove insoluble impurities under conditions when the insulin is rendered soluble.

The present invention achieves a reduction in the enzymatic digestion and host cell impurities associated with insulin following enzymatic digestion of pre-proinsulin by selective pH-dependent precipitation and solubilization of insulin. The process facilitates the exchange of insulin from one solution to another solution. The present invention is exemplified in the Examples for the purification of insulin glargine but may be used to in processes to purify any protein or peptide, including any insulin or insulin analog.

The present invention provides the use of two tandem microfiltration (MF) steps in a single downstream purification unit operation that functions to reduce both soluble and insoluble impurities from recombinant insulin or insulin analog and to exchange the recombinant insulin or insulin analog into a suitable buffer for downstream purification. In the first microfiltration step (MF1), the recombinant insulin or insulin analog is precipitated. This allows for its separation from soluble impurities such as host DNA, host cell protein (HCP), tryptic digestion by-products (e.g., cleaved C-peptide and N-terminal fusion) and residual trypsin via diafiltration during the microfiltration stage of the operation. The precipitated recombinant insulin or insulin analog is then concentrated and washed via diafiltration to reduce the amount of soluble impurities; the recombinant insulin or insulin analog remains as a precipitate on the retentate side of the membrane. In the second microfiltration step (MF2), the recombinant insulin or insulin analog is resolubilized and recovered in the permeate stream. Insoluble impurities are retained by the membrane, then concentrated and discarded with the retentate pool at the end of the step.

In the process for purifying insulin or insulin analog prior to downstream purification steps, product precipitation and batch centrifugation have been used to achieve impurity removal. The insulin or insulin analog product in the enzymatic digest pool is precipitated out of solution by adjusting the pH to a pH that effects precipitation of the insulin or insulin analog, the process stream is then centrifuged, and the supernatant fraction containing impurities soluble at the pH are decanted. The precipitate is then washed with buffer, re-centrifuged, and decanted again followed by one additional wash cycle. The precipitate is then resolublized by lowering the pH so that the material can be further purified in subsequent downstream chromatography steps. This process was sufficient for small scale production batches (less than 1000 L fermentation), but batch centrifugation is not a feasible option for larger scale production due to the physical size limitations of batch centrifuges.

The current invention provides a scaleable and improved means to purify recombinant insulin or insulin analog (product) from the enzymatic digest pool sufficiently during production. The present invention uses cross-flow microfiltration or diafiltration rather than batch centrifugation. The microfiltration may be performed by tangential flow filtration using a 0.1 μm pore size flat sheet membrane cassette (60 $m^2$ filter area) or hollow fiber cartridge and with a permeate pressure of at least about 3 or 5 psig or more (about 20.68 MPa to 34.47 MPa or more). The microfiltration is conducted in two stages: MF1—During this first stage, the product is precipitated by adjusting the pH to a PH sufficient to precipitate the product to provide a mixture of precipitated and soluble components that is then washed via diafiltration to reduce the amount of soluble residual trypsin and other peptide (C-peptide, N-terminal fusion) byproducts. The product remains as a precipitate on the retentate side of the membrane; MF2—During this second stage, the washed product is solubilized in place by adjusting the pH to a pH sufficient to solubilize the product and then gradually passing the solubilized product through to the permeate side of the membrane. Insoluble impurities are retained by the membrane and discarded.

In the MF1 step, insulin or insulin analog is precipitated out of solution by adjusting the pH of the enzymatic digest pool to a pH that effects precipitation of the insulin or insulin analog to provide a pH-adjusted aqueous mixture (precipitate pool) at a temperature around room temperature. For example, for insulin glargine, the enzymatic digest pool is adjusted to about pH 5.7 to 6.1, or about pH 5.9, which is sufficient to precipitate the insulin glargine in the digest pool, to provide the pH-adjusted aqueous mixture (precipitate pool). The trypsin and/or chymotrypsin used for the enzymatic digest are still soluble at this pH as are the cleaved C-peptide and leader sequence peptide, as are many other impurities arising from the enzymatic digestion and initial isolation of the pre-proinsulin or insulin analog from recombinant host cells. The precipitated insulin or insulin analog in the precipitate pool is concentrated to about two times the initial starting volume to provide a first retentate pool containing about 2 to 4 g insulin/L or about 3.25 g insulin/L. The first retentate pool is then recirculated through a 0.1 μm flat sheet membrane as the soluble impurities pass through the membrane and are removed from the retentate pool while the precipitated insulin or insulin analog is retained by the microfilter. The first retentate pool is washed with about up to two or four or more equivalent retentate pool volumes of MF1 buffer at the same pH as the pH of the retentate pool or a pH within about 1.5 pH units of the pH of the retentate pool or water to improve the purity by removing additional impurities and to provide a second retentate pool comprising the precipitated insulin or insulin analog and substantially reduced soluble impurities. For example, as shown in the Examples, precipitated insulin glargine may be washed with an MF1 buffer at about pH 6.9. Lab scale studies have also demonstrated that water may be used in place of buffer for diafiltration during the MF1 step. The matrix of the precipitated product may be serving as the primary buffering agent and the additional buffering capacity of the MF1 buffer may not be needed. Following the washes, the permeate flow is stopped but the precipitated product in the second retentate pool continues to recirculate across the surface of the microfilter.

In particular aspects, the MF1 buffer may be a citrate buffer or an acetate buffer. In particular aspects, the wash is performed by adding the water or MF1 buffer to the first retentate pool at a rate substantially the same as the rate the first retentate pool is permeating the microfilter for a time sufficient to substantially reduce the amount of soluble impurities in the first retentate pool to provide the second retentate pool. In particular aspects, the wash is performed by sequentially by diluting the first retentate pool with a predetermined volume of water of MF1 buffer and then permeating the diluted first retentate pool through the microfilter to reduce the volume to the initial volume of the first retentate pool for a number of cycles sufficient to substantially reduce the amount of soluble impurities in the first retentate pool to provide the second retentate pool.

In particular aspects, the wash is performed by batch or continuous diafiltration using water or MF1 buffer and then permeating the first retentate pool through the microfilter for a number of cycles sufficient to substantially reduce the amount of soluble impurities in the first retentate pool to provide the second retentate pool.

In the MF2 step, the precipitated insulin or insulin analog in the second retentate pool is solubilized by adjusting the pH of the second retentate pool to a pH that effects resolubilization of the insulin or insulin analog to provide a third retentate pool. The third retentate pool is recirculated through the same 0.1 μm tangential flow filtration flat sheet membrane or hollow fiber cartridge. For example, as shown in the Examples, insulin glargine may be solubilized by lowering the pH of the second retentate pool to about pH 2.9 to 3.3 or about pH 3.1. Titration may be achieved using a stock solution of HCl, e.g., 5N HCl. In particular embodiments, the precipitated insulin or insulin analog is resolubilized by adding acetate to a final concentration of about 50 to 70 mM, 58 to 62 mM, or about 60 mM to the second retentate pool and then titrating to a pH that affects resolubilization of the precipitated insulin or insulin analog to provide the third retentate pool. The third retentate pool is recirculated over the filter without permeate flow for time sufficient to substantially resolubilize the precipitated insulin or insulin analog. To increase resolubilization, the third retentate pool may be diluted 1× or 2× with MF2 buffer to provide a diluted third retentate pool. MF2 buffer may be an acetate solution and may be at the same pH as the third retentate pool. The diluted third retentate pool is recirculated over the filter without permeate flow for a time sufficient to solubilize the precipitated insulin or insulin analog.

Following recirculation, product recovery is started by resuming permeate flow through the filter. The permeate comprising the resolubilized insulin or insulin analog passes through the membrane and is collected as a permeate pool comprising solubilized product while insoluble impurities (e.g., residual host cell proteins) are retained on the microfilter. The permeation is performed until the diluted third retentate pool is concentrated up to about two times or four times or more of the initial third retentate starting volume to produce a concentrated third retentate pool and the concentrated third retentate pool is then washed with up to about six or more equivalent volumes of MF2 buffer to maximize recovery of the insulin or insulin analog through the membrane and which is collected in the permeate pool. The process is capable of providing solubilized product pool that has a purity of 70-75% compared to the initial enzymatic digest pool purity of 40-45% as measured by reverse-phase HPLC assay. This purity is more than sufficient for the subsequent downstream purification steps to handle and allows for insulin or insulin analog production to be scaled up to larger than 10,000 L fermentation batches.

In particular aspects, the wash is performed by adding the MF2 buffer to the concentrated third retentate pool at a rate substantially the same as the rate the pool is permeating the microfilter for a time sufficient to substantially recover the solubilized insulin or insulin analog. In particular aspects, the wash is performed by sequentially by diluting the concentrated third retentate pool with a predetermined volume of water of MF2 buffer and then permeating through the microfilter to reduce the volume to the initial volume of the concentrated third retentate pool for a number of cycles sufficient to substantially recover the solubilized insulin or insulin analog.

A number of different organic acids, including acetic acid and citric acid, may be used as buffering agent during the microfiltration. In the example of insulin glargine, prior to microfiltration, the insulin glargine molecule is enzymatically digested to remove the leader sequence and C-peptide. This digestion includes protection of lysine residues via citraconylation (see for example, U.S. Published Patent Application 20120214965). After completion of the digest, citraconyl groups are liberated via addition of about 150 mM organic acid (either citric or acetic have been used) and acidification to about pH 2.4 using hydrochloric acid. This deprotected product is then adjusted to about pH 5.9 for microfiltration as described above.

Initially, citric acid was used as the principle organic acid to quench the enzymatic digest as well as the buffering agent during diafiltration in MF1. However, when the process was scaled up for commercial manufacture, it was found that high viscosity of the pH-adjusted aqueous mixture was found to reduce robustness and negatively impact operability of the step at large scale. The inventors found that using acetic acid instead of citric acid (or other organic acids) in the process reduced the viscosity of the precipitated pool dramatically, thereby improving the overall operability of the MF1 step and increasing achievable loading of the microfilter. Accordingly, in particular embodiments of the present invention, acetic acid is used as the principal organic acid to quench the enzymatic digest as well as the buffering agent during diafiltration in MF1 and MF2.

In a further embodiment, the retained pool in the MF2 step containing the solubilized insulin or insulin analog following pH adjustment is diluted up to two times the initial volume of the retained pool following pH adjustment with MF2 buffer. It had been observed that full scale yields may be significantly lower than the yields that had been observed at laboratory and pilot scales. However, the inventors found that dilution of the retained pool following pH adjustment to about two times the initial retained pool volume following pH adjustment resulted in yields similar to the yields that had been expected based upon laboratory and pilot scale yields. This impact may be attributed to scale-dependent factors such as flow path tortuosity, pumping regime, and particle characteristics of the precipitated product stream.

The present invention further includes monitoring the two tandem microfiltration step using a process analytical technology (PAT). In particular embodiments, the performance of the tandem microfiltration step is monitored using ultraviolet absorbance, high performance liquid chromatography (HPLC), or ultra-high performance chromatography (UHPLC). In particular aspects the PAT is used as described in Example 3.

The following examples are intended to promote a further understanding of the present invention.

EXAMPLE 1

Microfiltration of Insulin Glargine using Citrate-based Buffer is described.

Objective:

The precipitation of insulin glargine from the digest pool allows for its separation from soluble impurities such as host DNA, HCP, tryptic digestion by-products (e.g., cleaved C-peptide and N-terminal fusion) and residual trypsin via diafiltration during the microfiltration stage of the operation. Following filtration, the insulin glargine is resolubilized by acidification before further processing by cation exchange (CEX) chromatography.

Microfiltration (MF) Description:

This step is conducted in two stages: microfiltration step 1 (MF1)—During this first stage, the precipitated product is concentrated and washed via diafiltration to reduce residual trypsin and other trypsin related by-products (C-peptide, N-terminal fusion). The product remains as a precipitate on the retentate side of the membrane; microfiltration step 2 (MF2)—During this second stage, the washed product is solubilized in place using acetic acid and hydrochloric acid and then gradually passed through to the permeate side of the membrane. Insoluble impurities are retained by the membrane then concentrated and discarded with the retentate at the end of the step. Microfiltration is performed by tangential flow filtration using a 0.1 μm pore size flat sheet membrane cassette (60 m$^2$ filter area) or hollow fiber cartridge.

Description:

Insulin glargine precursor, which has been properly folded in a refold reaction, is citraconylated and then digested with trypsin to provide insulin glargine. After digestion is complete, the reaction is stopped by first adding acetic acid to achieve a concentration of 150 mM acetate, and then the pH is adjusted to pH 2.4 using HCl and incubated for about four hours to provide a digest pool.

MF1:

The Digest Pool is then titrated to pH 5.9 with concentrated NaOH. The NaOH concentration is not critical, though care should be taken to not allow pockets of high pH to form during the pH adjustment. Approximately 0.33 moles of NaOH per kg of digest pool is needed for the pH adjustment. Insulin product and some impurities will precipitate out of solution at around pH 5.0. The precipitated pool mixes for 15 minutes. The precipitated pool is then concentrated to 6 g/L by tangential flow filtration using a 0.1 μm membrane cassette. The concentrated precipitate pool is then diafiltered while maintaining constant volume for four diafiltration volumes using microfiltration step 1 (MF1) buffer containing 20 mM sodium citrate, pH 6.9. After four diafiltration volumes, the permeate flow is stopped.

MF2:

The product is resolubilized in the microfilter skid by adding concentrated acetic acid to a pool concentration of 40 mM acetic acid and titrating the pool to pH 3.3 using stock HCL solution. The resolubilized pool is recirculated on the membrane for 15 minutes with no permeate flow to solubilize product held up in the MF system. The retentate tank is then drained and collected and 5 L/m$^2$ of 150 mM acetic acid is added to tank. The permeate line is drained to waste to remove residual citrate in the line and then directed to the retentate tank for total recirculation. The acetic acid is recirculated for two hours at high trans-membrane pressure (TMP) to regenerate and resolubilize all remaining product in the system and on the membranes. The product is then transferred back to the retentate tank to start the resolubilization microfiltration step 2 (MF2). Permeate flow is resumed and collected while the resolubilized pool is concentrated 4× by volume. The concentrated resolubilized pool is diafiltered for six diafiltration volumes using MF2 buffer containing 50 mM acetic acid and the permeate stream is collected as product. After six diafiltration volumes, the permeate flow is stopped. The permeate pool is filtered through a 0.22 μm filter at a loading of 750 L/m$^2$. The concentrated retentate pool is discarded as waste. The membrane is flushed with 500 mM acetic acid and cleaned with 0.1N NaOH for storage and reuse.

EXAMPLE 2

Microfiltration of Insulin Glargine using Acetate-based Buffer is described.

Objective:

The precipitation of insulin glargine from the digest pool allows for its separation from soluble impurities such as host DNA, HCP, tryptic digestion by-products (e.g., cleaved C-peptide and N-terminal fusion) and residual trypsin via diafiltration during the microfiltration stage of the operation. Following filtration, the insulin glargine is resolubilized by acidification before further processing by cation exchange (CEX) chromatography.

Microfiltration (MF) Description:

This step is conducted in two stages: microfiltration step 1 (MF1)—During this first stage, the precipitated product is concentrated and washed via diafiltration to reduce residual trypsin and other trypsin related by-products (C-peptide, N-terminal fusion). The product remains as a precipitate on the retentate side of the membrane; microfiltration step 2 (MF2)—During this second stage, the washed product is solubilized in place using acetic acid and hydrochloric acid and then gradually passed through to the permeate side of the membrane. Insoluble impurities are retained by the membrane then concentrated and discarded with the retentate at the end of the step. Microfiltration is performed by tangential flow filtration using a 0.1 µm pore size flat sheet membrane cassette (60 m² filter area) or hollow fiber cartridge.

Description:

Insulin glargine precursor, which has been properly folded in a refold reaction, is citraconylated and then digested with trypsin to provide insulin glargine. After digestion is complete, the reaction is stopped by first adding acetic acid to achieve a concentration of 150 mM acetate, and then the pH is adjusted to pH 2.4 using HCl to and incubated for about four hours to provide a Digest Pool.

MF1:

The digest pool is slowly titrated to pH 5.9 with 50% (w/v) NaOH. The NaOH concentration is not critical, though care should be taken to add the base in a high shear mixing zone so as not to allow pockets of high pH to form during the pH adjustment. Product and some impurities will precipitate out of solution at pH ~5.0. During pH adjustment, high mixing speed is required to ensure complete mixing and to avoid gel formation. Mixing of the precipitated pool is continued after pH adjustment for at least 15 minutes. Next, the precipitated pool is concentrated to a target concentration of 3.25 g insulin glargine/L. Note that a more dilute solution equates to improved filtration performance. The retentate is then diafiltered at constant retentate volume for at least two diafiltration volumes using MF1 buffer containing 20 mM sodium acetate, pH 6.9. After two or more diafiltration volumes of MF1 buffer, the permeate flow is stopped, but the precipitated product continues to recirculate across the membrane, to provide the retentate pool. During MF1, the permeate flows directly to drain and is not collected.

MF2:

The product is resolubilized in the MF skid by adding acetic acid to increase the retentate pool acetate concentration by 40 mM thus achieving a final concentration of approximately 60 mM acetate. The pool is then titrated to pH 3.1 using a stock 5N HCl solution to complete the resolubilization. Again, care is taken to introduce the HCl at a high shear mixing zone to avoid pockets of low pH during pH adjustment. Following the pH adjustment, the resolubilized pool is recirculated for a minimum of 15 minutes with no permeate flow. The batch is then diluted, up to 2×, with MF2 buffer containing 50 mM acetic acid to maximize resolubilization. Retentate recirculation is then resumed for a minimum of 15 minutes. To start the product recovery, permeate flow is resumed and directed to the collection vessel while the resolubilized pool is concentrated at least 2× by volume. The concentrated resolubilized pool is diafiltered continuously with 6 diafiltration volumes, at constant retentate volume, using MF2 buffer containing 50 mM acetic acid and the permeate stream continues to be collected as product. After all diafiltration volumes have been collected, MF2 buffer addition is stopped. At this point, the retentate pool can be concentrated to the minimum operating volume of the process tank to maximize product recovery. After confirming sufficient step yield in the Permeate Product Pool (an in-process sample is submitted for insulin glargine concentration determination by RP-UPLC-48 analysis), the concentrated retentate pool is discarded as waste.

EXAMPLE 3

Process analytical technology (PAT) may be used for improving consistency of MF processes and enabling more efficient scale-up (Rathore et al. 2010a). PAT methods encompass a broad range of analytical technologies that may be deployed on the manufacturing floor to provide real-time process monitoring for feed-forward and feed-back control as well as improved process consistency. In particular, high performance liquid chromatography (HPLC) and ultra high performance liquid chromatography (UPLC) based methods have been implemented in downstream purification processes to provide real-time concentration or purity measurements. These data have been used to inform chromatography pooling decisions (Rathore et al. 2010b; Rathore et al. 2008), control chromatography loading factors (Fahrner and Blank 1999), and ensure consistency of tertiary structure in oligomeric protein preparations (Barackman et al. 2004).

Figure 1B:
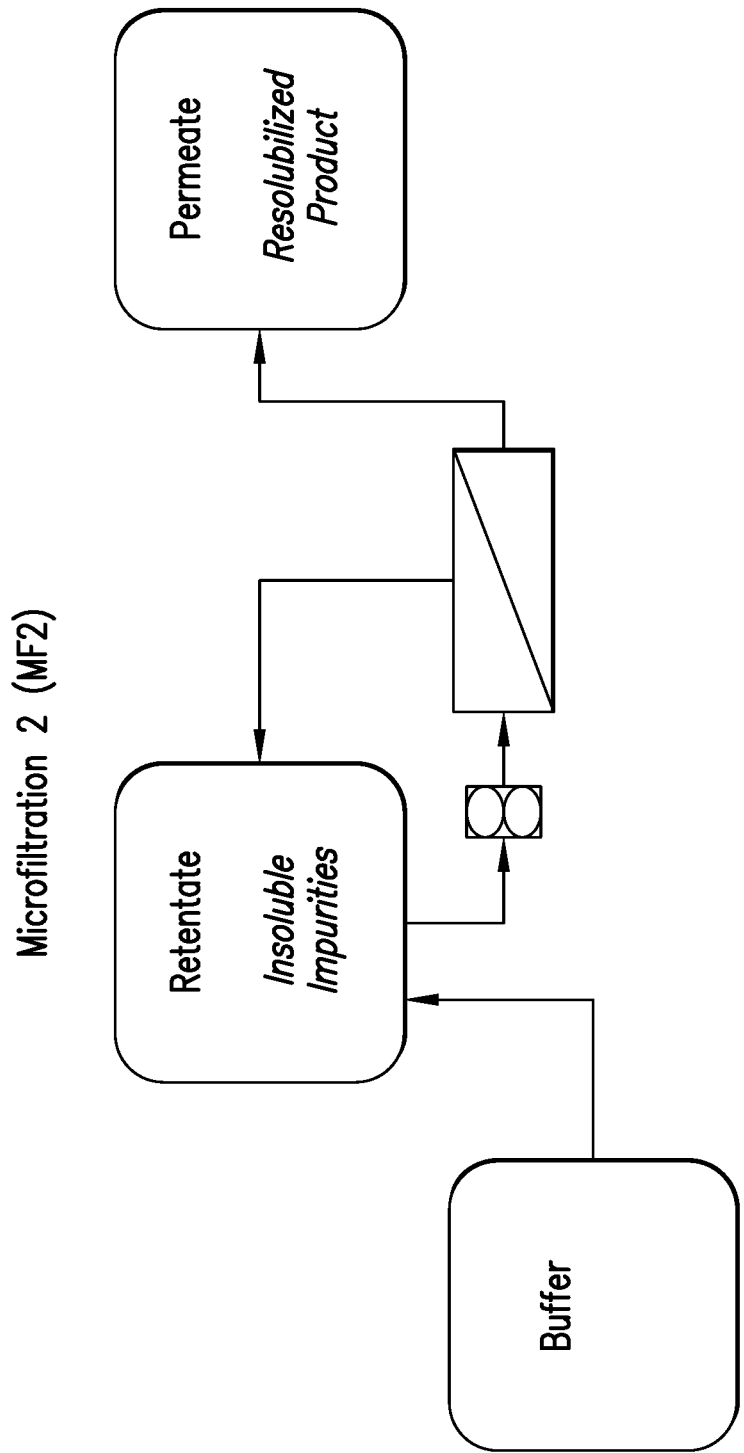

In this example, UPLC-based PAT was used to facilitate successful scale-up of a microfiltration process used in the downstream purification of a recombinant protein. In this process, two tangential flow microfiltration (MF) steps are performed in tandem to remove impurities (FIG. 1). In the first microfiltration step (MF1), the protein product is precipitated. The precipitated protein is then concentrated and washed via diafiltration to reduce soluble impurities; the product remains as a precipitate on the retentate side of the membrane. In the second microfiltration step (MF2), the protein product is resolubilized and recovered in the permeate stream. Insoluble impurities are retained by the membrane, then concentrated and discarded with the retentate at the end of the step.

Figure 2:
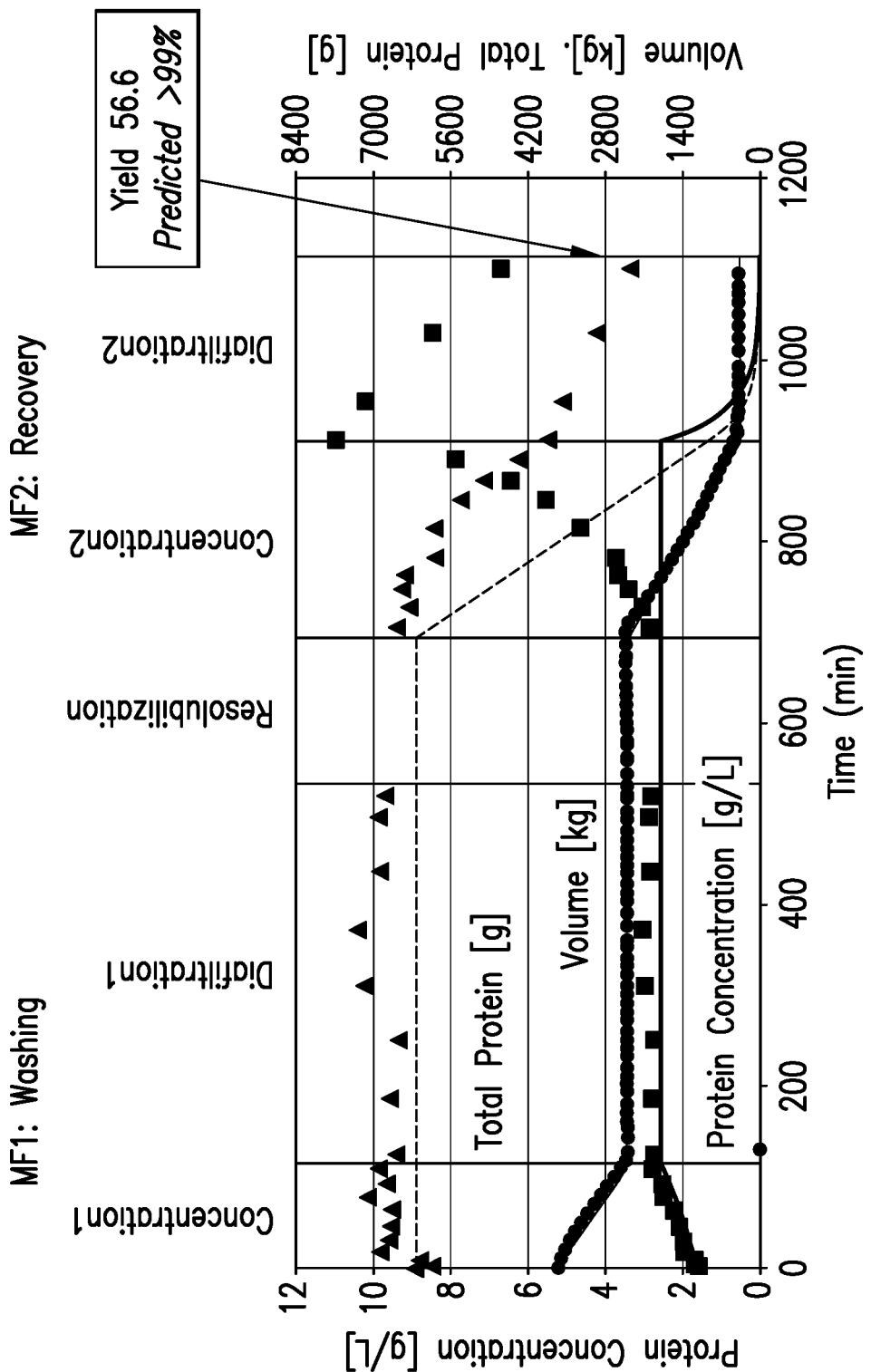
FIG. 2. Performance of the baseline microfiltration process. Mass balance based modeling and at-line PAT were deployed to improve understanding of microfiltration step consistency. MF2 performance deviated significantly from the model, exemplified by poor product recovery during diafiltration.
Figure 3:
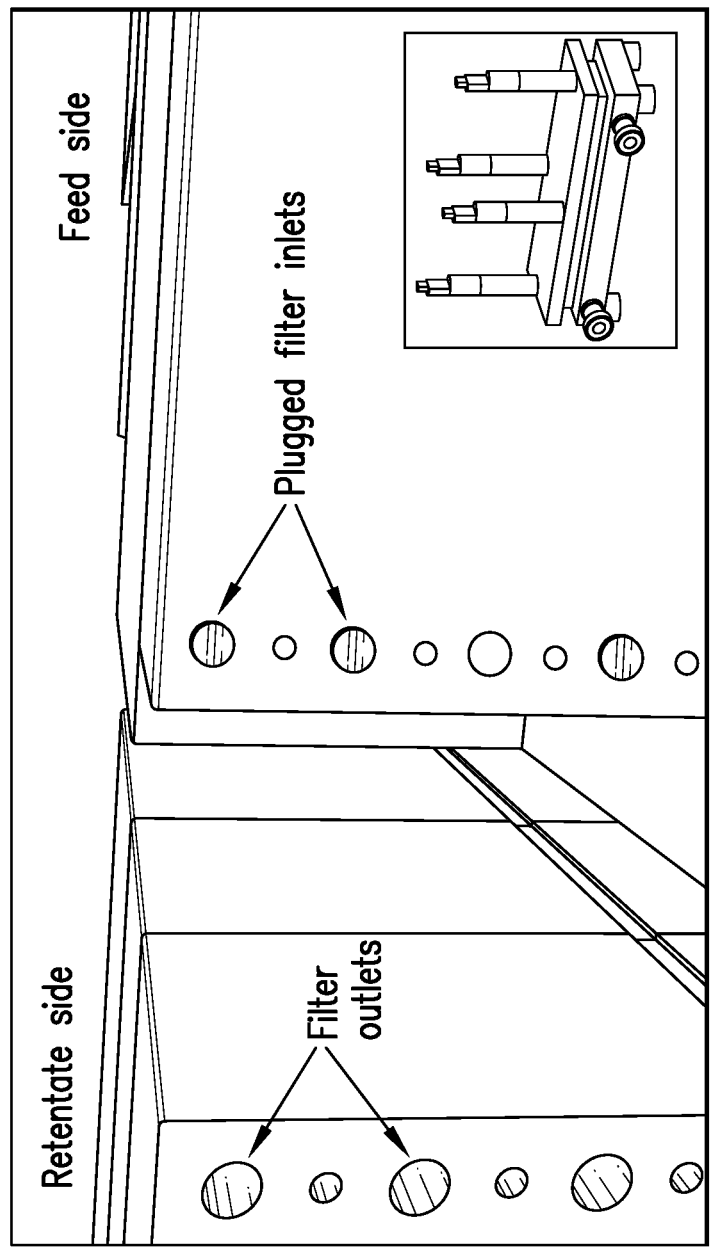
FIG. 3. Example of microfiltration filter fouling. A fouled microfiltration membrane from a full scale batch performed prior to optimization. Membrane fouling is evident at the inlets of filter cassettes. For context, a microfiltration cassette in a laboratory scale MF assembly is shown in the insert.
Figure 4A:
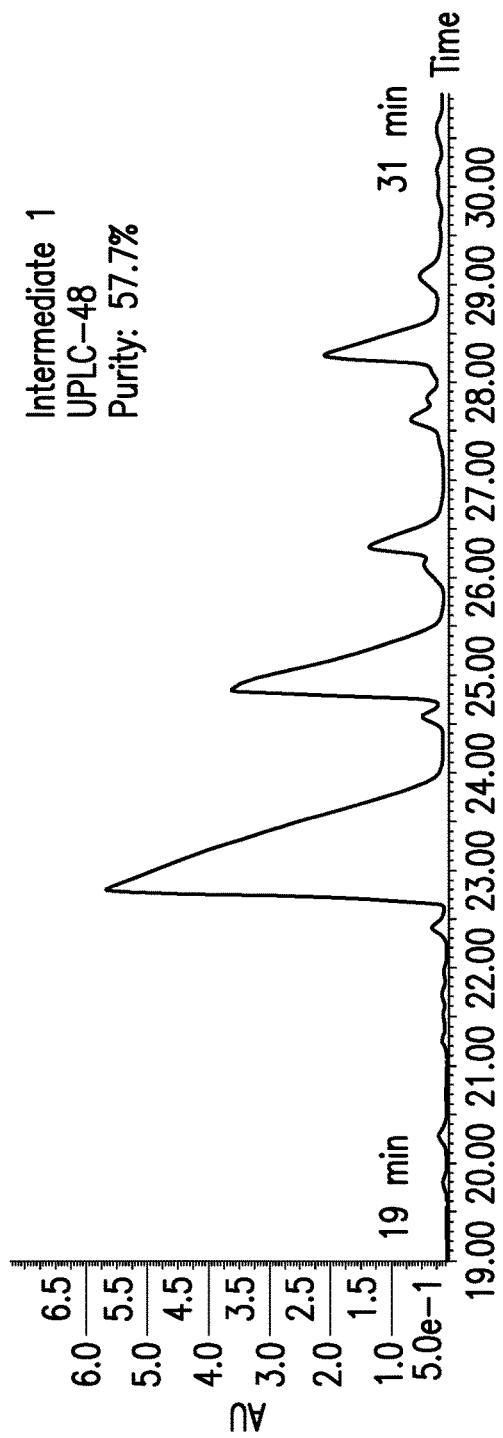
FIG. 4A, FIG. 4B, FIG. 4C, and FIG. 4D. Impurity resolution of PAT method. Impurity resolution in two product intermediates (FIGS. 4A and 4C) by an established 48 minute RP-UPLC method and a newly developed 10 minute RP-UPLC method (FIGS. 4B and 4C.
Figure 4B:
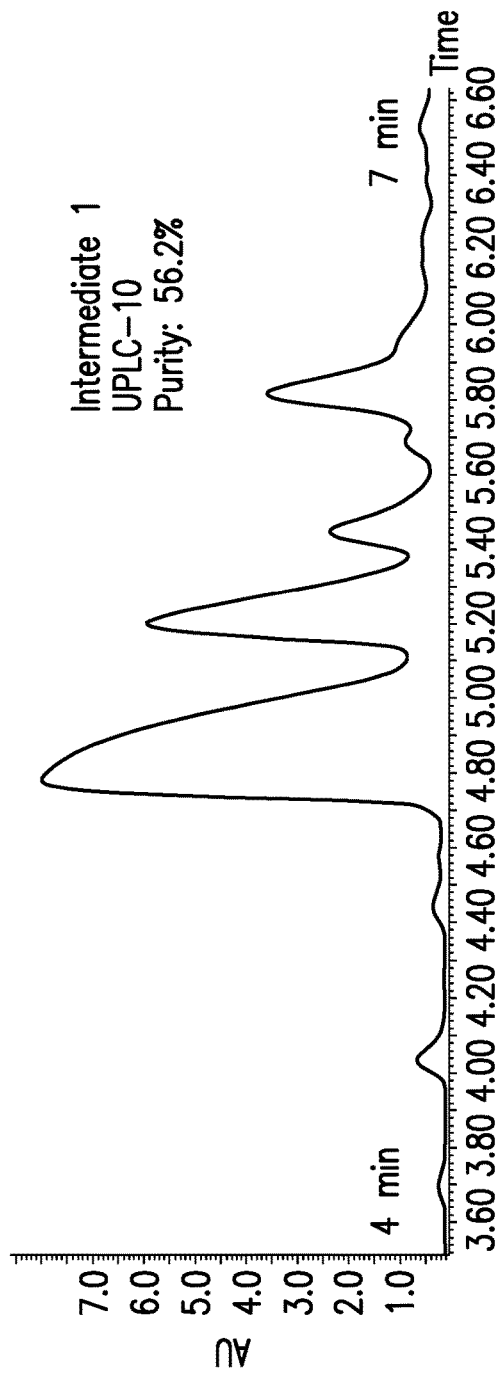
Figure 4C:
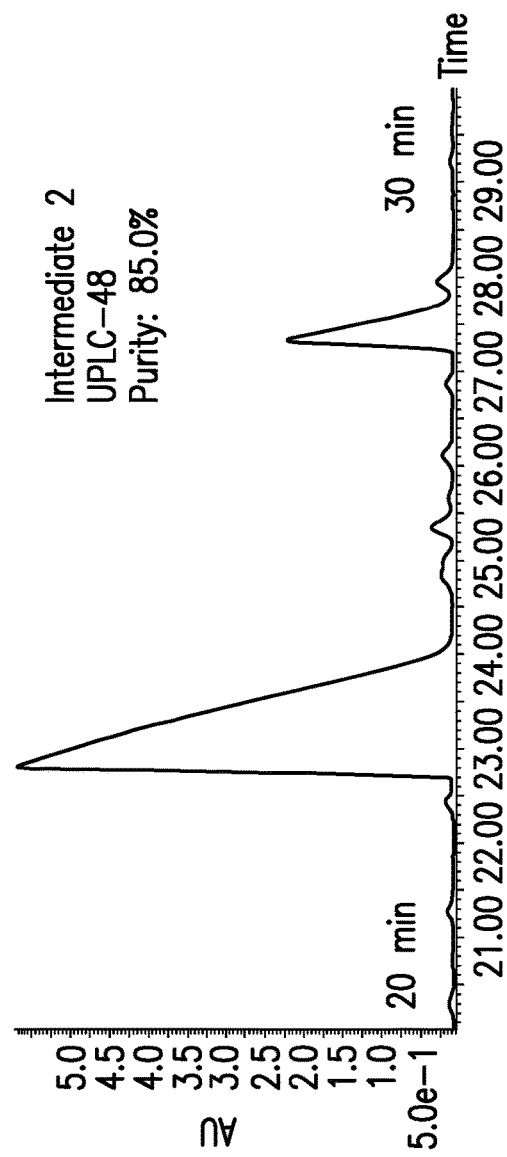
Figure 4D:
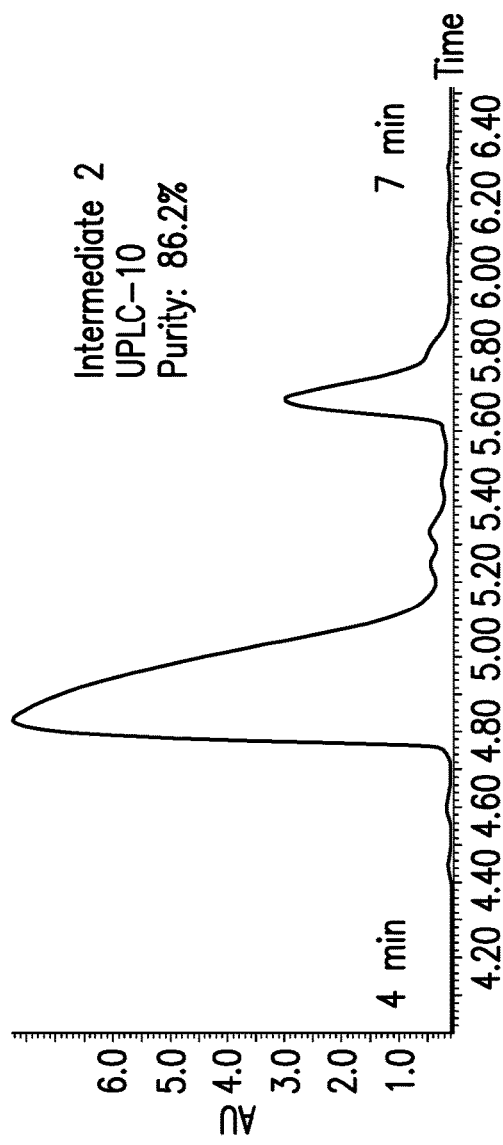

The tandem MF process is further illustrated in FIG. 2, which depicts the performance of a typical MF operation (before optimization), indicating the respective concentration, diafiltration, and resolubilization phases. At laboratory scale, 80% product recovery is consistently attained. However, upon scale up using classical parameters (Table 1), process yields declined to 50-70% (56.6% in the example shown in FIG. 2). Moreover, significant filter fouling occurred, including visually observable clogging of filter inlets (FIG. 3). However, we developed a UPLC based PAT tool and deployed it to provide real-time process monitoring, then compared these data to a mass balance based model of ideal filtration performance. The results were used to develop operational changes that restored process yields to >90%, in alignment with historical experience at laboratory scale. This paradigm for PAT-driven risk mitigation should be broadly applicable toward improved process understanding and efficient scale-up of biopharmaceutical filtration processes.

TABLE 1

Key parameters and targets for microfiltration scale-up.

| Parameter | Units | Target Value | Acceptable Range |
|---|---|---|---|
| Load Factor (MF1) | g/m² | 135 | 75-140 |
| Crossflow Rate (MF1 and MF2) | L/min/m² | 9 | 8-10 |
| Transmembrane Pressure (MF1) | psi | <20 | ≤25 |
| Transmembrane Pressure (MF2) | psi | <15 | ≤25 |

Methods

Microfiltration is performed by tangential flow using a 0.1 µm pore size flat sheet membrane cassette (Pall Supor). Total filter area is scale 20-600× from laboratory and pilot scale to full scale. New filters are flushed with water to remove vendor supplied storage agents, sanitized with sodium hydroxide, and stored in storage solution until use. Filters also may be regenerated after use. Both new and regenerated filters are subjected to a normalized water permeability (NWP) measurement (target ≥50 LMH/psig) and a filter integrity test (target ≤2 psig drop over 2 minutes at ≥10 psig) prior to use in the process.

Immediately before initiation of MF1, filters are flushed with water to remove the storage solution, then flushed with equilibration buffer and held wetted with buffer until the start of processing. The protein product pool is titrated to reduce the pH to the target level to achieve product precipitation. Mixing of the precipitated pool is continued after pH adjustment for a minimum of 15 minutes. Next, the precipitated product is concentrated to a pre-set target volume while the permeate stream is directed to waste. The retentate is then diafiltered at constant retentate volume for at least 2 diafiltration volumes using diafiltration buffer, with the permeate stream again directed to waste. After at least 2 diafiltration volumes, the permeate flow is stopped, but the precipitated product continues to recirculate across the membrane.

During MF2, the product is resolubilized by acidification to a target pH. Following the pH adjustment, the resolubilized protein product is recirculated for a minimum of 15 minutes with no permeate flow. To start product recovery, permeate flow is resumed and directed to the collection vessel while the volume of the retentate (containing resolubilized protein product) is reduced at least 2×. The concentrated product is then diafiltered for 6 diafiltration volumes, at constant retentate volume, using MF2 buffer, while the permeate stream continues to be collected as product. After all diafiltration volumes have been collected, buffer addition is stopped and the concentrated retentate is discarded as waste.

Modeling.

A mass balance based model of protein concentration in the retentate was employed to further understand microfiltration performance (Kovacs et al. 2008; Lutz and Raghunath 2007; Marichal-Gallardo and Alvarez 2012). The change in volume of the retentate can be expressed as a function of the addition of buffer, $u(t)$, and removal of permeate, $q(t)$:

$$\frac{dV_R(t)}{dt} = u(t) - q(t)$$

The mass balance of protein product concentration in the retentate, $C_R(t)$, and permeate, $C_P(t)$, streams can then be expressed as:

$$\frac{dy}{dx} V_R(t) C_R(t) = -q(t) C_P(t)$$

The retentate and permeate protein concentrations can be further related by a Retention factor, $R(t)$, representing the fraction of protein retained by the membrane:

$$C_P(t) = C_R(t)(1 - R(t))$$

After substitution and rearrangement, the following differential equation is obtained:

$$\frac{dC_R(t)}{dt} V_R(t) = C_R(t)(R(t)q(t) - u(t)) \quad (1)$$

A general solution for concentration can be derived from equation (1) with the following assumptions and boundary conditions applied:

$u(t)=0$ (no buffer addition)

$C_R(0)=C_0$ $V_R(0)=V_0$

In the absence of buffer addition, the change in volume of the feed tank can be expressed as:

$$\frac{dV_R(t)}{dt} = -q(t)$$

After substitution and rearrangement, equation (1) can be expressed as:

$$\frac{dC_R(t)}{C_R(t)} = -R(t) \frac{dV_R(t)}{V_R(t)}$$

After integrating and solving for boundary conditions, the following equation is obtained:

$$C_R(t) = C_0 \left(\frac{V_0}{V_R(t)}\right)^{R(t)} \quad (2)$$

In the case of MF1 concentration, Retention is assumed to be 1 (insoluble product fully retained by the membrane), giving:

MF1 Concentration $$C_R(t) = \frac{C_0 V_0}{V_R(t)} \quad (3)$$

In the case of MF2 concentration, Retention is assumed to be 0 (complete permeability of soluble protein), giving:

MF2 Concentration $C_R(t)=C_0$ \quad (4)

A general solution for constant volume diafiltration can be derived from equation (1) with the following assumptions and boundary conditions applied:

$$\frac{dC_R(t)}{dt} = N(t) C_R(t)[R(t) - 1]$$

After substitution and rearrangement, equation (1) can be expressed as:

$V_R(t) = V_0$ (constant retentate volume)

$N(t) = \frac{u(t)}{V_0}$ (number of diafiltration volumes applied)

$C_R(0) = C_0$

After integrating and solving for boundary conditions the following equation is obtained:

$$C_R(t) = C_0 e^{N(t)[R(t)-1]} \quad (5)$$

In the case of MF1 diafiltration, Retention is assumed to be 1 (insoluble product completely retained by the membrane), giving:

MF1 Diafiltration $C_R(t)=C_0$

In the case of MF2 diafiltration, Retention is assumed to be 0 (complete permeability of soluble protein), giving:

MF2 Diafiltration $C_R(t)=C_0 e^{-N(t)}$ (6)

In the optimized process employing batch diafiltration prior to MF2, the model was updated accordingly.

UPLC Methods

An RP-UPLC based PAT method was developed to monitor protein concentration during processing. The PAT method was adapted from a previously developed 48 minute RP-UPLC method, which utilized a 2.1×150 mm column (Waters Acquity BEH Shield C18 1.7 µm, Catalog #186003376) and a gradient of 27 to 33% acetonitrile over 28 minutes. To enable real time at-line monitoring, this method was modified to reduce total assay time to 10 minutes. Both methods employed water/acetonitrile/trifluorotriacetic acid gradients at a flow rate of 0.2 mL/min and were performed on Waters H-Class UPLC instruments. Method development consisted of scouting combinations of column length, stationary phase, and gradient to achieve optimal separation of specific product impurities. The newly developed method utilized a 2.1×50 mm column (Waters Acquity BEH C18 1.7 µm, Catalog #186002350) and a gradient of 31 to 33% acetonitrile over 5 minutes.

Host Cell Protein ELISA

A commercially available ELISA kit (Cygnus Technologies, Catalog #F410) was used to determine residual host cell protein content of MF protein product. Testing was performed according to the manufacturer's instructions. A host cell protein preparation derived from the same strain used to produce the recombinant protein, but lacking the expression vector, was used as a calibrator in the assay.

Statistical analysis. Statistical significance was assessed by analysis of variance and two-tailed Student's t test. Differences were considered significant if they exhibited p values <0.05 in the Student's t test. Data analyses were performed using Microsoft Excel and JMP.

Results

PAT method development. A rapid, accurate, and precise method was needed to determine protein concentration throughout the MF process and to assess performance relative to model derived expectations. A previously developed RP-UPLC based assay had been used to monitor protein concentration and purity during MF. However, the long turnaround time of this method (48 minutes) was prohibitive for use as an at-line PAT method. Thus, the method was modified with a shorter column and compressed gradient to achieve a total assay time of less than 10 minutes. The newly developed method gave comparable chromatography to the existing 48 minute method, as shown for two representative protein intermediate sample types in FIG. 4. Although overall purity values were comparable between the two methods, there is a modest reduction in impurity resolution in the shorter method, as seen in the Figure.

Figure 5A:
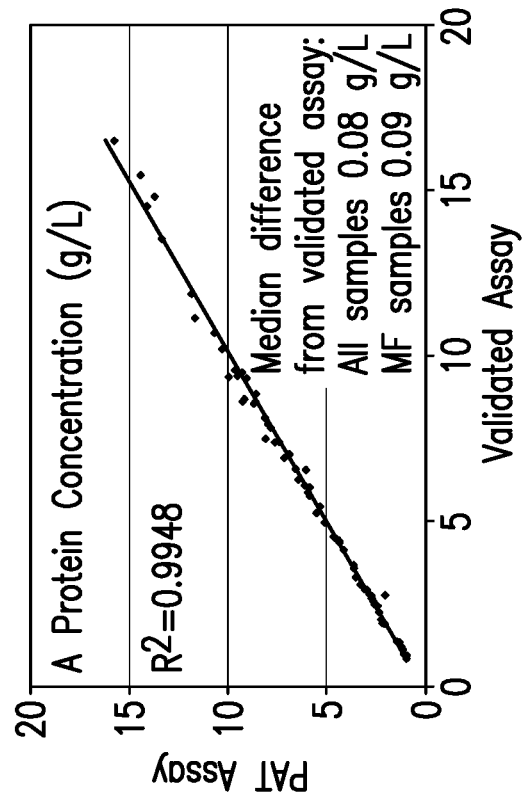
FIG. 5A and FIG. 5B. Comparability of PAT method and validated methods. The PAT method performed comparably to previously validated methods for determination of concentration (FIG. 5A, 73 samples) and purity (FIG. 5B, 66 samples).
Figure 5B:
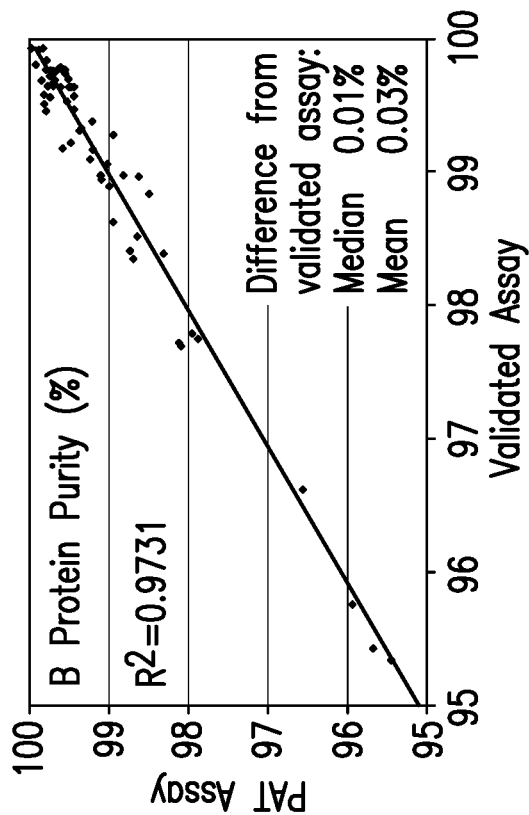

The method was successfully validated for measurement of both concentration and purity, with all protocol acceptance criteria being met. Validation characteristics for concentration measurement are summarized in Table 2 (validation characteristics for purity measurement not shown). To establish comparability of the 10 RP-UPLC minute method with established methods, comparative testing of a large number of samples was performed. When compared to a previously validated RP-HPLC method, measured concentration values over a range of 0.9 g/L to 15.8 g/L were well correlated between the two methods (R2=0.99) and exhibited a median difference of 0.08 g/L (FIG. 5A). The differences between methods were attributed to discrepancies in sample handling and storage due to the large number of samples tested and the time period over which the testing was completed. Subsequent comparisons using fewer samples under more controlled conditions resulted in even smaller differences (data not shown). Purity values also agreed well between the 10 minute and 48 minute RP-UPLC methods (FIG. 5B), with most differences arising from loss of resolution of minor impurity peaks in highly purified samples (>98%). Based on a successful validation and demonstration of comparability to established methods, the 10 minute RP-UPLC method was considered suitable for use as a PAT tool to monitor protein concentration during MF processing.

TABLE 2

Validation characteristics of a 10 minute RP-UPLC based PAT method.

| Characteristic | Sample Type 1 | Sample Type 2 | Sample Type 3 |
| --- | --- | --- | --- |
| Specificity (interfering peaks) | None | None | None |
| Accuracy (% recovery) | 99-102 | 97-101 | 99-101 |
| Precision (% RSD) | 0 | 0 | 0 |
| Linearity ($r^2$) | 1.00 | 1.00 | 1.00 |
| Range (µg column load) | 1.6-4.7 | 1.9-5.7 | 1.9-5.6 |

Process optimization. A mass balance based model predicted that >99% of protein product would be recovered at the conclusion of the MF2 process. At laboratory scale, greater than 80% recovery is consistently achieved (Table 3). However, upon scale up, process yields fell to 50-70%. UPLC based at-line PAT testing showed that MF1 performance aligned with model derived predictions (FIG. 2). Retentate protein concentration increased linearly during the MF1 concentration phase as volume was reduced; retentate protein concentration then remained constant throughout MF1 diafiltration. The protein thus remained insoluble during MF1 and was completely retained by the filter membrane (Retention factor=1). Although some modest operational adjustments to initial crossflow ramp rate and permeate flux were implemented to mitigate fouling in MF1, the data in this study indicate that MF1 performs as expected at full scale and thus is not limiting for successful scale-up.

TABLE 3

Comparison of microfiltration performance at laboratory scale and full scale.

| Attribute | Lab Scale n = 3 | Full Scale Pre-Optimization n = 4 | Full Scale Post-Optimization n = 10 |
| --- | --- | --- | --- |
| Step Yield (%) | 80 ± 7 | 64 ± 6 | 93 ± 4 |
| Product Purity (%)* | 89 ± 2 | 93 ± 1** | 92 ± 1 |
| Host Cell Proteins (ng/mL) | 12 ± 2 | 32 ± 15 | 26 ± 6 |

*Measured following a subsequent purification step;
**n = 3 for Product Purity only In contrast to MF1, performance during MF2 deviated considerably from model expectations. Protein concentration was expected to remain constant during MF2 concentration as the volume of the retentate is reduced and soluble protein is collected in the permeate stream. However, the data indicate that retentate protein concentration actually increased dramatically, from 2.8 g/L to 11.0 g/L at the conclusion of the MF2 concentration phase. Retentate protein concentration also declined slower than expected during MF2 diafiltration, resulting in significant residual product in the retentate after completion of the target number of diafiltration volumes. Step optimization efforts were therefore focused on MF2.

Figure 6:
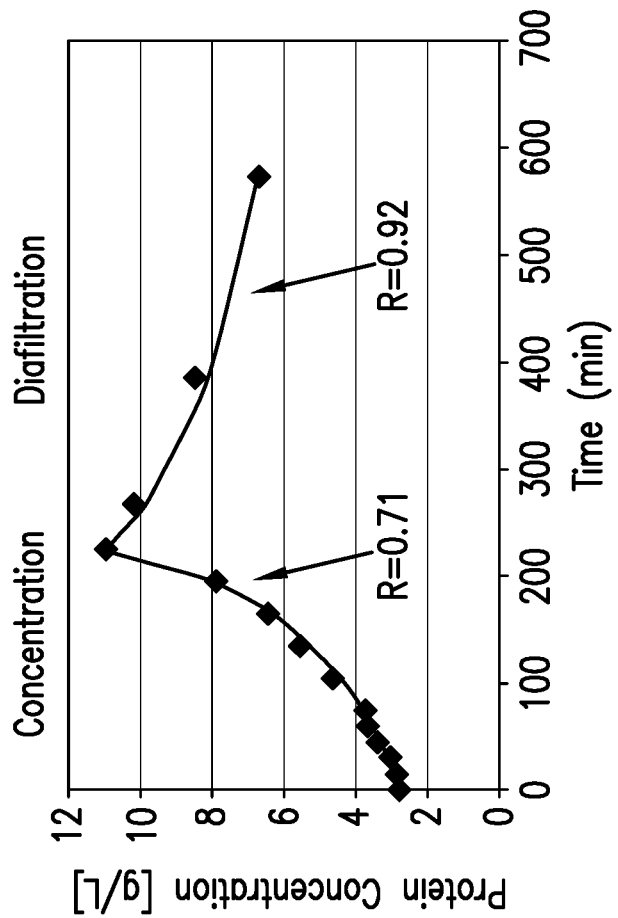
FIG. 6. Updated mass balance model reflecting non-ideal membrane permeability in MF2. Retention factors of 0.71 and 0.92 were found to best fit the experimental data for MF2 concentration and MF2 diafiltration, respectively, indicating that the assumption of complete membrane permeability was incorrect.

The poor product recovery observed during MF2 called into question the assumption of complete membrane permeability (R=0 in the model) of resolubilized protein product. Fitting actual MF2 data to equations (2) and (5) gave Retention factors of 0.71 and 0.92 during MF2 concentration and diafiltration, respectively, indicating that membrane permeability was actually far lower than predicted (FIG. 6). Reduced membrane permeability is indicative of fouling, decreased protein solubility, or both. We focused our optimization efforts on the possibility that incomplete dissolution of precipitated protein during the acid resolubilization phase after MF1 was limiting recovery in MF2. This explanation was consistent with the increasing protein levels observed during MF2 concentration; if precipitated protein product (unable to flow through to the permeate stream) continues to redissolve as total volume is reduced, protein concentration would increase.

Figure 7:
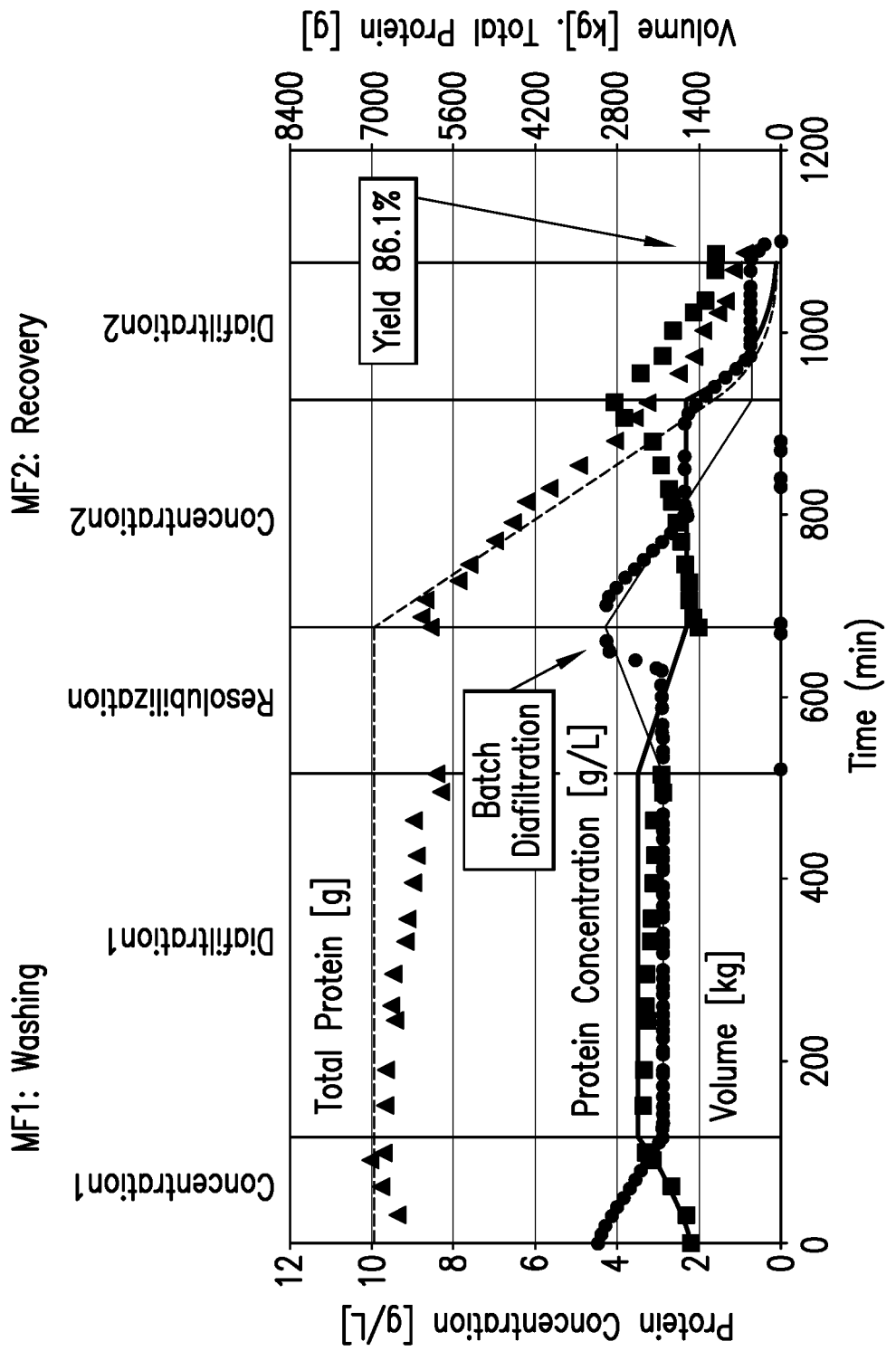
FIG. 7. Performance of optimized microfiltration step. Process yields increased approximately 30% after implementation of batch diafiltration prior to the start of MF2.
Figure 8:
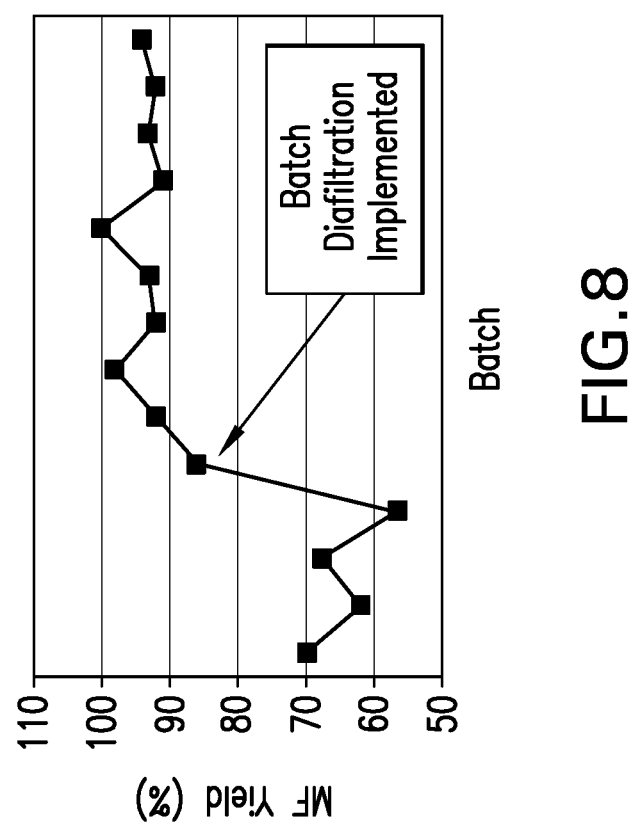
FIG. 8. Microfiltration control chart. Microfiltration yield increased from 64±6% before optimization to 93±4% after optimization (process change indicated with arrow).

Simply increasing the number of diafiltration volumes in MF2 may not be a preferred option for increasing product recovery due to cycle time concerns, cost constraints, or volume limitations further downstream in the purification process. As an alternative, the product was diluted up to 2× prior to MF2 to aid in resolubilization, thus converting a portion of the MF2 diafiltration process to batch mode. When the modified process was performed with at-line PAT monitoring, protein concentration during MF2 aligned more closely with model expectations (FIG. 7). Although protein concentration did increase modestly during the MF2 concentration phase, it did not exceed 4.0 g/L, as compared with a maximum value of 11.0 g/L in the unoptimized process. Fitting data from the modified process to equations (2) and (5) gave Retention factors of 0.42 and 0.72 during concentration and diafiltration, respectively, indicating that membrane permeability increased considerably in the modified MF2 process. This improvement resulted in significantly improved recovery (86.1% in the example shown in FIG. 7), bringing process yields in line with laboratory scale experience (Table 3). In addition, the improvement was consistent over time, as shown in FIG. 8. Importantly, this change did not adversely impact product purity or clearance of impurities (Table 3).

Discussion

Although the microfiltration process was scaled using classical parameters (Table 1), yields were observed to decline approximately 30% at full scale (FIG. 2 and Table 3). By implementing batch diafiltration prior to MF2, the efficiency of protein resolubilization was improved and protein recovery was restored to levels comparable with historical process experience. Some factors that influence filter fouling and filtration scale-up efficiency are specific to the process, while others arise from the unique physicochemical properties of the protein (and non-protein) constituents in the feedstock.

Scale-dependent MF factors include those that impact fluid flow and thus may alter the solubility properties of both product and impurities present in the feedstock (Kim et al. 1993; Maa and Hsu 1997). For example, there are physical differences in the flow path arising from the configuration of filters in a full scale filter bank compared with a single filter cassette in a laboratory scale filter assembly. A second difference relates to the impact of pumping on fluid flow. Laboratory scale models often utilize peristaltic pumps, which generate pulsatile flow. In contrast, full scale processes employ continuous flow pumps such as rotary lobe pumps. Collectively, these differences can impact flow regimes, microcavitation, shear, and other aspects of fluid dynamics (Kim et al. 2001; van Reis and Zydney 2007).

Process parameters that influence particle characteristics of the feedstock are another potential source of scale-up inconsistency. Physical differences in insoluble particulate matter may affect interaction with the filter membrane, thus influencing filter fouling (Belfort et al. 1994; Maruyama et al. 2001). In our case, the protein precipitation process performed at full scale could generate an altered particle size distribution relative to that observed at laboratory scale due to differences in agitation or rate of base addition. Differences in particle characteristics may affect the rate of resolubilization and thus product recovery during MF2. More routine characterization of particle size distribution and other attributes of solids loads in MF feedstocks by methods such as laser diffraction would be helpful as a standard component of the scale-up toolkit (Wisniewski and Grasmick 1998).

In addition to these process-specific factors, the physical and biochemical properties of the feedstock must be considered. For example, solubility is determined by biochemical properties (isoelectric point, hydrophobicity, and molecular weight) and can thus be manipulated by corresponding process parameters such as buffer pH, operating temperature, and concentration. Changes in solubility may also require compensating adjustments to microfiltration parameters such as transmembrane pressure, crossflow velocity, and filter loading to mitigate fouling.

Mass balance based models such as the one presented here can aid in de-risking process scale-up (Lutz and Raghunath 2007; van Reis and Zydney 2007). Although our model framework was able to identify deviations from ideal performance, future work may address limitations in some of the model's underlying assumptions. First, it is assumed that the portion of product retained by the filter membrane (Retention factor in the model) is fixed at either 0 or 1 depending on the state of the protein (precipitated or in solution). In practice, this number likely falls somewhere in between, as our data showed. In addition, Retention factors may change over time during processing as filters progressively foul (Ho and Zydney 2000), although in our case constant Retention factors provided an excellent fit for the experimental data (FIG. 6). Second, it is assumed that permeate flux is constant over time, whereas in practice flux declines as membrane resistance increases, and TMP is increased within allowable operating ranges to compensate and restore target flux. Thus, a more sophisticated model may provide even greater process understanding in some cases.

The use of PAT monitoring should be broadly applicable for increasing efficiency when scaling filtration processes. In addition to the example presented here, other opportunities to reduce cycle time or improve process consistency include product recovery during traditional primary recovery MF processes and removal of specific product impurities during ultrafiltration. In addition to monitoring product and impurities, PAT methods can be developed to monitor other attributes such as host residuals, process residuals, and buffer salts. However, some filtration processes may not be amenable to HPLC or UPLC based PAT monitoring. This may be due to the speed of processing, limited opportunities for sampling, or complexity of sample matrices. In these situations, retrospective testing may be used to correlate product concentration (or purity) with a surrogate metric that is more readily monitored in-line or on-line, such as pH. In one example, pH monitoring was proposed to reduce the number of diafiltration volumes in an ultrafiltration process, impacting both cost and cycle time (Rathore et al. 2010a). Similarly, conductivity monitoring could be appropriate for salt mediated protein precipitation and subsequent resolubilization.

REFERENCES

Barackman J, Prado I, Karunatilake C, Furuya K. 2004. Evaluation of on-line high-performance size-exclusion chromatography, differential refractometry, and multi-angle laser light scattering analysis for the monitoring of the oligomeric state of human immunodeficiency virus vaccine protein antigen. Journal of Chromatography A 1043(1):57-64.

Belfort G, Davis R H, Zydney A L. 1994. The Behavior of Suspensions and Macromolecular Solutions in Cross-Flow Microfiltration. Journal of Membrane Science 96(1-2):1-58.

Bentham A C, Ireton M J, Hoare M, Dunnill P. 1988. Protein Precipitate Recovery Using Microporous Membranes. Biotechnology and Bioengineering 31(9):984-994.

Bramaud C, Aimar P, Daufin G. 1997. Whey protein fractionation: Isoelectric precipitation of alpha-lactalbumin under gentle heat treatment. Biotechnology and Bioengineering 56(4):391-397.

Fahrner R L, Blank G S. 1999. Real-time control of antibody loading during protein A affinity chromatography using an on-line assay. Journal of Chromatography A 849(1):191-196.

Gagnon P. 2012. Technology trends in antibody purification. Journal of Chromatography A 1221:57-70.

Ge X, Trabbic-Carlson K, Chilkoti A, Filipe C D M. 2006. Purification of an elastin-like fusion protein by microfiltration. Biotechnology and Bioengineering 95(3):424-432.

Ho C C, Zydney A L. 2000. A combined pore blockage and cake filtration model for protein fouling during microfiltration. Journal of Colloid and Interface Science 232(2):389-399.

Kim J S, Lee C H, Chang I S. 2001. Effect of pump shear on the performance of a crossflow membrane bioreactor. Water Research 35(9):2137-2144.

Kim K J, Chen V, Fane A G. 1993. Some Factors Determining Protein Aggregation during Ultrafiltration. Biotechnology and Bioengineering 42(2):260-265.

Kovacs Z, Discacciati M, Samhaber W. 2008. Numerical simulation and optimization of multi-step batch membrane processes. Journal of Membrane Science 324(1-2):50-58.

Lutz H, Raghunath B. 2007. Ultrafiltration Process Design and Implementation. In: Shukla A A, Etzel M R, and Gadam S, Editor. Process Scale Bioseparations for the Biopharmaceutical Industry: 297-332.

Maa Y F, Hsu C C. 1997. Protein denaturation by combined effect of shear and air-liquid interface. Biotechnology and Bioengineering 54(6):503-512.

Marichal-Gallardo P A, Alvarez M M. 2012. State-of-the-art in downstream processing of monoclonal antibodies: process trends in design and validation. Biotechnol Prog 28(4): 899-916.

Maruyama T, Katoh S, Nakajima M, Nabetani H, Abbott T P, Shono A, Satoh K. 2001. FT-IR analysis of BSA fouled on ultrafiltration and microfiltration membranes. Journal of Membrane Science 192(1-2):201-207.

McDonald P, Victa C, Carter-Franklin J N, Fahrner R. 2009. Selective Antibody Precipitation Using Polyelectrolytes: A Novel Approach to the Purification of Monoclonal Antibodies. Biotechnology and Bioengineering 102(4):1141-1151.

Palacio L, Ho C C, Zydney A L. 2002. Application of a pore-blockage—Cake-filtration model to protein fouling during microfiltration. Biotechnology and Bioengineering 79(3):260-270.

Rathore A S, Bhambure R, Ghare V. 2010a. Process analytical technology (PAT) for biopharmaceutical products. Analytical and Bioanalytical Chemistry 398(1):137-154.

Rathore A S, Parr L, Dermawan S, Lawson K, Lu Y F. 2010b. Large Scale Demonstration of a Process Analytical Technology Application in Bioprocessing: Use of On-line High Performance Liquid Chromatography for Making Real Time Pooling Decisions for Process Chromatography. Biotechnology Progress 26(2):448-457.

Rathore A S, Wood R, Sharma A, Dermawan S. 2008. Case Study and Application of Process Analytical Technology (PAT) Towards Bioprocessing: II. Use of Ultra-Performance Liquid Chromatography (UPLC) for Making Real-Time Pooling Decisions for Process Chromatography. Biotechnology and Bioengineering 101(6):1366-1374.

Roush D J, Lu Y F. 2008. Advances in primary recovery: Centrifugation and membrane technology. Biotechnology Progress 24(3):488-495.

Saxena A, Tripathi B P, Kumar M, Shahi V K. 2009. Membrane-based techniques for the separation and purification of proteins: An overview. Advances in Colloid and Interface Science 145(1-2):1-22.

Taipa M A, Kaul R H, Mattiasson B, Cabral J M S. 2000. Recovery of a monoclonal antibody from hybridoma culture supernatant by affinity precipitation with Eudragit S-100. Bioseparation 9(5):291-298.

Thommes J, Etzel M. 2007. Alternatives to chromatographic separations. Biotechnology Progress 23(1):42-45.

van Reis R, Zydney A. 2001. Membrane separations in biotechnology. Current Opinion in Biotechnology 12(2):208-211.

van Reis R, Zydney A. 2007. Bioprocess membrane technology. Journal of Membrane Science 297(1-2):16-50.

Venkiteshwaran A, Heider P, Teyssevre L, Belfort G. 2008. Selective Precipitation-Assisted Recovery of Immunoglobulins From Bovine Serum Using Controlled-Fouling Crossflow Membrane Microfiltration. Biotechnology and Bioengineering 101(5):957-966.

Wisniewski C, Grasmick A. 1998. Floc size distribution in a membrane bioreactor and consequences for membrane fouling. Colloids and Surfaces a-Physicochemical and Engineering Aspects 138(2-3):403-411.

Table of Sequences

| SEQ ID NO: | Description | Sequence |
|---|---|---|
| 1 | Human insulin A chain | GIVEQCCTSICSLYQLENYCN |
| 2 | Human insulin B chain | FVNQHLCGSHLVEALYLVCGE RGFFYTPKT |
| 3 | Insulin glargine A chain | GIVEQCCTSICSLYQLENYCG |
| 4 | Insulin glargine B chain | FVNQHLCGSHLVEALYLVCGE RGFFYTPKTRR |

-continued

Table of Sequences

| SEQ ID NO: | Description | Sequence |
|---|---|---|
| 5 | Insulin lispro B chain | FVNQHLCGSHLVEALYLVCGE RGFFYTKPT |
| 6 | Insulin glusiline B chain | FVKQHLCGSHLVEALYLVCGE RGFFYTPET |

-continued

Table of Sequences

| SEQ ID NO: | Description | Sequence |
|---|---|---|
| 7 | Insulin aspart B chain | FVNQHLCGSHLVEALYLVCGE RGFFYTDKT |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A process for producing insulin or insulin analog, wherein the process has a digestion step in which an aqueous solution of properly refolded pre-proinsulin or pre-proinsulin analog is digested with one or more proteolytic enzymes to produce an aqueous solution of insulin or insulin analog, digestion byproducts, and host cell impurities and a downstream purification or chromatography step, in which the insulin or insulin analog is separated from the digestion byproducts, and host cell impurities, wherein the improvement comprises performing two tandem microfiltration steps subsequent to the digestion step and prior to the downstream purification or chromatography step, wherein the two tandem microfiltration steps comprise a first microfiltration step in which the insulin or insulin analog is precipitated from a first aqueous solution and retained by a microfilter and soluble impurities are permeated through the microfilter and a second microfiltration step in which the insulin or insulin analog retained by the microfilter is solubilized into a second aqueous solution and the solubilized insulin or insulin analog is permeated through the microfilter.

2. The process of claim 1, wherein (a) the first microfiltration step comprises:

(i) adjusting the pH of the aqueous solution from the digestion step to a pH sufficient to precipitate the insulin or insulin analog from the aqueous solution to provide an aqueous mixture comprising precipitated insulin or insulin analog and soluble and precipitated digest related impurities and host-cell impurities;

(ii) applying the aqueous mixture to a surface of a microfilter having a pore exclusion size sufficient to retain the precipitated insulin or insulin analog thereto to provide a first retentate pool; and (iii) permeating the soluble impurities that are smaller than the exclusion pore size of the microfilter through the microfilter while washing the first retentate pool with water or a first aqueous solution at a pH that is at or within 1.5 pH units of the pH of the pH-adjusted aqueous mixture for a time sufficient to substantially remove the soluble impurities from the first retentate pool to provide a second retentate pool; and
(b) the second microfiltration step comprises:
  (i) adding a second aqueous solution to the second retentate pool and adjusting the pH to a pH sufficient to solubilize the precipitated insulin or insulin analog to provide a third retentate pool and
  (ii) permeating the third retentate pool comprising the solubilized insulin or insulin analog through the microfilter wherein insoluble impurities and impurities larger than the exclusion pore size of the microfilter are retained by the microfilter and a permeate pool comprising the solubilized insulin or insulin analog is collected to produce the insulin or insulin analog.

3. The process of claim 1, wherein the microfilter is a tangential flow flat sheet or hollow fiber microfilter.

4. The process of claim 1, wherein the insulin is native human, porcine, or bovine insulin and wherein the insulin analog is an acid-stable insulin analog or a pI-shifted insulin analog in which the pI of the insulin analog is less than or greater than the pI of native human insulin or wherein the insulin analog is insulin glargine, insulin aspart, insulin glulisine, or insulin lispro.

5. The process of claim 2, wherein the first and second aqueous solutions comprise acetic acid or wherein the first aqueous solution comprises citric acid and the second aqueous solution comprises acetic acid.

6. A process for producing insulin or insulin analog, comprising:
(a) providing an aqueous solution of properly folded and enzymatically digested pre-proinsulin or pre-proinsulin analog comprising a mixture of insulin or insulin analog, digest related impurities and host-cell impurities;
(b) adjusting the pH of the aqueous solution to a pH sufficient to effect precipitation of the insulin or insulin analog from the aqueous solution to provide an aqueous mixture containing precipitated insulin or insulin analog and soluble and precipitated digest related impurities and host-cell impurities;
(c) applying the aqueous mixture to a surface of a microfilter having an exclusion pore size sufficient to retain the precipitated insulin or insulin analog thereto to provide a first retentate pool;
(d) permeating the first retentate pool through the microfilter to remove the soluble digest related impurities and host-cell impurities from the precipitated insulin or insulin analog retained by the microfilter while adding water or a first aqueous solution at a first pH that is at or within 1.5 pH unit of the pH of the pH-adjusted aqueous mixture to the retentate pool at a rate that is substantially the same as the rate the first retentate pool is permeating through the microfilter and for a time sufficient to substantially reduce the amount of the soluble digest related impurities and host-cell impurities in the first retentate pool to provide a second retentate pool;
(e) adding a second aqueous solution to the second retentate pool and adjusting the pH to a second pH sufficient to solubilize the precipitated insulin or insulin analog and to provide a third retentate pool; and
(f) permeating the third retentate pool through the microfilter for a time sufficient to reduce the volume of the third retentate pool to produce a reduced-volume third retentate pool while collecting the permeate comprising the solubilized insulin or insulin analog to provide a permeate pool; and
(g) permeating the reduced-volume third retentate pool through the microfilter into the permeate pool while adding a third aqueous solution at a pH that is at or within 1.5 pH unit of the second pH to the reduced-volume third retentate pool at a rate that is substantially the same as the rate the reduced-volume third retentate pool is permeating through the microfilter for a time sufficient to substantially recover the solubilized insulin or insulin analog in the reduced-volume third retentate pool; wherein the permeate pool provides the insulin or insulin analog.

7. The process of claim 6, wherein the microfilter is a tangential flow flat sheet or hollow fiber microfilter.

8. The process of claim 6, wherein the insulin is native human, porcine, or bovine insulin and/or wherein the insulin analog is an acid-stable insulin analog or a pI-shifted insulin analog in which the pI of the insulin analog is less than or greater than the pI of native human insulin or wherein the insulin analog is insulin glargine, insulin aspart, insulin glulisine, or insulin lispro.

9. The process of claim 6, wherein the first and second aqueous solutions comprise acetic acid or wherein the first aqueous solution comprises citric acid and the second aqueous solution comprises acetic acid.

10. The process of claim 6, wherein the first retentate pool is washed with at least one, two, three, or four first retentate pool volumes of the water or first aqueous solution.

11. The process of claim 6, wherein the reduced-volume third retentate pool is washed with at least one, two, three, four, five, or six reduced-volume third retentate pool volumes of the third aqueous solution at a pH that is at or within 1.5 pH unit of the second pH.

12. A process for producing insulin or insulin analog, comprising:
(a) providing an aqueous solution of properly folded and enzymatically digested pre-proinsulin or pre-proinsulin analog comprising a mixture of insulin or insulin analog, digest related impurities and host-cell impurities;
(b) adjusting the pH of the aqueous solution to a pH sufficient to effect precipitation of the insulin or insulin analog from the aqueous solution to provide an aqueous mixture containing precipitated insulin or insulin analog and soluble and precipitated digest related impurities and host-cell impurities;
(c) applying the aqueous mixture to a surface of a microfilter having an exclusion pore size sufficient to retain the precipitated insulin or insulin analog thereto to provide a first retentate pool;
(d) sequentially diluting the first retentate pool with a predetermined volume of water or a first aqueous solution at a first pH that is at or within 1.5 pH unit of the pH of the pH-adjusted aqueous mixture and permeating the diluted first retentate pool through the microfilter to remove the soluble digest related impurities and host-cell impurities from the precipitated insulin or insulin analog retained by the microfilter for a number of cycles sufficient to substantially reduce the amount of the soluble digest related impurities and host-cell impurities in the first retentate pool to provide a second retentate pool;
(e) adding a second aqueous solution to the second retentate pool and adjusting the pH to a second pH sufficient to solubilize the precipitated insulin or insulin analog and to provide a third retentate pool; and (f) permeating the third retentate pool through the microfilter for a time sufficient to reduce the volume of the third retentate pool to produce a reduced-volume third retentate pool while collecting the permeate comprising the solubilized insulin or insulin analog to provide a permeate pool; and (g) sequentially diluting the reduced-volume third retentate pool with a predetermined volume of a third aqueous solution at a pH that is at or within 1.5 pH unit of the second pH to the reduced-volume third retentate pool and permeating the reduced-volume third retentate pool through the microfilter into the permeate pool for a number of cycles sufficient to substantially recover the solubilized insulin or insulin analog in the reduced-volume third retentate pool; wherein the permeate pool provides the insulin or insulin analog.

13. The process of claim 12, wherein the microfilter is a tangential flow flat sheet or hollow fiber microfilter.

14. The process of claim 12, wherein the insulin is native human, porcine, or bovine insulin and/or wherein the insulin analog is an acid-stable insulin analog or a pI-shifted insulin analog in which the pI of the insulin analog is less than or greater than the pI of native human insulin or wherein the insulin analog is insulin glargine, insulin aspart, insulin glulisine, or insulin lispro.

15. The process of claim 12, wherein the first and second aqueous solutions comprise acetic acid or wherein the first aqueous solution comprises citric acid and the second aqueous solution comprises acetic acid.

* * * * *

SEQUENCE LISTING

```
<160> NUMBER OF SEQ ID NOS: 7

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Insulin glargine A chain

<400> SEQUENCE: 3

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 4
<211> LENGTH: 32
<212> TYPE: PRT
<213> ORGANISM: Artificial Sequence
<220> FEATURE:
<223> OTHER INFORMATION: Insulin glargine B chain

<400> SEQUENCE: 4

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Pro Lys Thr Arg Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Insulin lispro B chain

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Insulin glulisine B chain

<400> SEQUENCE: 6

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Insulin aspart B chain

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```